United States Patent
Sutherland et al.

(10) Patent No.: US 7,155,316 B2
(45) Date of Patent: Dec. 26, 2006

(54) MICROSURGICAL ROBOT SYSTEM

(75) Inventors: Garnette Roy Sutherland, Calgary (CA); Deon Francois Louw, Calgary (CA); Paul Bradley McBeth, Calgary (CA); Tim Fielding, Brampton (CA); Dennis John Gregoris, Toronto (CA)

(73) Assignee: Microbotics Corporation, Calgary (CA)

( * ) Notice: Subject to any disclaimer, the term of this patent is extended or adjusted under 35 U.S.C. 154(b) by 296 days.

(21) Appl. No.: 10/639,692

(22) Filed: Aug. 13, 2003

(65) Prior Publication Data

US 2004/0111183 A1 Jun. 10, 2004

Related U.S. Application Data

(60) Provisional application No. 60/402,724, filed on Aug. 13, 2002.

(51) Int. Cl.
G06F 19/00 (2006.01)
(52) U.S. Cl. .................. 700/248; 700/256; 700/247; 700/248; 700/249; 700/258; 700/259; 700/264; 600/102; 600/130; 606/130; 606/205; 318/568.11; 901/1; 901/2; 901/9
(58) Field of Classification Search ........ 700/245–249, 700/258–264; 600/102, 130; 606/205, 130, 606/139; 318/568.11; 901/1–2, 9; 414/1–2
See application file for complete search history.

(56) References Cited

U.S. PATENT DOCUMENTS 5,408,409 A 4/1995 Glassman et al.
5,624,398 A 4/1997 Smith et al.

(Continued)

FOREIGN PATENT DOCUMENTS

WO WO93/13916 7/1999
WO WO99/58055 11/1999

OTHER PUBLICATIONS

Mack, Minimally invasive and robotic surgery, 2001, Internet, p. 568-572.*

(Continued)

*Primary Examiner*—Thomas G. Black
*Assistant Examiner*—McDieunel Marc
(74) *Attorney, Agent, or Firm*—Adrian D. Battison; Michael R. Williams; Ryan W. Dupuis

(57) ABSTRACT

A robot system for use in surgical procedures has two movable arms each carried on a wheeled base with each arm having a six of degrees of freedom of movement and an end effector which can be rolled about its axis and an actuator which can slide along the axis for operating different tools adapted to be supported by the effector. Each end effector including optical force sensors for detecting forces applied to the tool by engagement with the part of the patient. A microscope is located at a position for viewing the part of the patient. The position of the tool tip can be digitized relative to fiducial markers visible in an MRI experiment. The workstation and control system has a pair of hand-controllers simultaneously manipulated by an operator to control movement of a respective one or both of the arms. The image from the microscope is displayed on a monitor in 2D and stereoscopically on a microscope viewer. A second MRI display shows an image of the part of the patient the real-time location of the tool. The robot is MRI compatible and can be configured to operate within a closed magnet bore. The arms are driven about vertical and horizontal axes by piezoelectric motors.

23 Claims, 18 Drawing Sheets

U.S. PATENT DOCUMENTS

| | | |
|---|---|---|
| 6,244,809 B1 | 6/2001 | Wang et al. |
| 6,684,129 B1* | 1/2004 | Salisbury et al. ........... 700/245 |
| 6,839,612 B1* | 1/2005 | Sanchez et al. ............ 700/245 |
| 6,852,107 B1* | 2/2005 | Wang et al. .................... 606/1 |
| 2003/0144649 A1* | 7/2003 | Ghodoussi et al. ............ 606/1 |

OTHER PUBLICATIONS

Hayashibe et al., Laser-pointing endoscope system for intra-operative 3D geometric registration, 2001, Internet, p. 1-6.*

Bate et al., The feasibility of force control over the Internet, 2001, Internet, p. 1-6.*

Vuskovic et al., Realistic force feedback for virgual reality based diagnostic surgery, 2000, IEEE, p. 1592-1598.*

* cited by examiner

MICROSURGICAL ROBOT SYSTEM

This application claims priority under 35 U.S.C. 119 from U.S. Provisional Application Ser. No. 60/402,724 filed Aug. 13, 2002.

BACKGROUND OF THE INVENTION

Complication avoidance in microsurgery (neurosurgery, ophthalmology, otorhinolaryngology, limb and digit reattachment) is crucial, and minimizes patient morbidity and health care costs. Current operative techniques rely on human surgeons, who have variable skill and dexterity. They also have physiological limits to their precision, tactile sensibility and stamina. Furthermore, the precise localization of brain pathology and neural structures is often difficult to achieve during surgery due to brain shifts and deformations as the operation progresses. While Intra-operative Magnetic Resonance Imaging (iMRI) has been used to monitor brain deformations, the surgeon currently has no effective way to use the iMRI data to enhance the precision and dexterity of surgery. They are compelled to rely on old techniques, and do not take advantage of these exquisite, updated images. Consequently, the quality of the surgery and outcomes is variable, and too often sub-optimal.

Surgical robots have the potential to increase the consistency and quality of neurosurgery, and when used in conjunction with the advanced diagnostic imaging capabilities of iMRI, can offer dramatic improvements. Unfortunately, there are no surgical robots that provide the surgeon with an ambidextrous and precise surgical system that uses updated iMRI patient data to achieve accurate image-guided surgery. In addition, there is no surgical robot with force sensing technology that is compatible with MRI systems.

Traditional surgery relies on the physician's surgical skills and dexterity and ability to localize structures in the body. Surgical robots have recently been developed to address the physical human issues such as fatigue and tremor in procedures. These systems were specifically developed for Minimally Invasive Surgery (MIS) or "key-hole" general surgery, orthopaedics and stereotactic neurosurgery.

The Intuitive Surgical Inc. da Vinci and Computer Motion ZEUS robots are examples of MIS robots. MIS robots are not suitable for neurosurgery since they require a portal in the body and lack the required dexterity and ability to reposition to different surgical worksites. Furthermore, neither system is MR compatible nor is there any force feedback capability. One patent on this development is U.S. Pat. No. 6,394,998 of Wallace et al issued May 28$^{th}$ 2002.

The da Vinci system is archetypal for general surgical robots. It has an articulated endowrist at the end of its two 7 mm diameter 'working' arms. A more stable camera arm with two lenses (allowing stereoscopic images) is also inserted through an 8 mm portal. The end-effectors can manipulate instruments with tips as small as 2 mm. They have seven degrees of freedom (three at the wrist). The surgeon controls the robot through a console placed in the operating room, allowing control of both the external and internal surgical environments. The surgeon's interface has instrument controllers that can filter tremor and decrease the scale of motion. Foot pedals expand the surgeon's repertoire, allowing tissue coagulation and irrigation. Visual feedback is through a proprietary stereoscopic display, called Surgical Immersion™. FDA approval has been obtained for thoracoscopic, abdominal and prostate procedures. Over one hundred da Vinci systems have been sold, and have been used to perform cholecystectomies, Nissen fundoplications, adrenalectomies, nephrectomies, mitral valve repairs, coronary artery bypass grafting and prostatectomies.

Surgical robots in orthopaedics may be classified as positioning or machining aids. Robodoc, used for hip replacement surgery, is an example of the latter. Again, they lack the dexterity, MR compatibility and force sensing needed for neurosurgery. The first-generation Robodoc was developed by IBM and the University of California Davis campus. The system was initially tested on 26 dogs in 1990. A second-generation Robodoc was built by Integrated Surgical Systems, and human trials conducted. In contrast, Kienzle developed a positioning device for total knee replacement (TKR). It locates the tibia and femur, and correctly positions the drill guide for the surgeon. Guide blocks are inserted into the drill holes, allowing the surgeon to accurately prepare the patient's bones for joint implantation. A similar system, named the Acrobot, has been developed by the Imperial College group and is designed for accurate machining of bone surfaces in TKR surgery. All the systems mentioned depend on preoperatively placed fiducial markers. Patents on this development are U.S. Pat. Nos. 5,695,500; 5,397,323 (both Taylor) U.S. Pat. No. 5,086,401; and U.S. Pat. No. 5,408,409 (both Glassman) issued in 1992 to 1997.

Robots designed for neurosurgical applications are generally restricted to positioning and holding instruments for simple procedures such as stereotactic biopsies.

In 1991, Drake reported the use of a PUMA 200 robot as a neurosurgical retractor in the resection of six thalamic astrocytomas. It is the same machine that was first used by Kwoh in 1985 to perform stereotactic biopsies. The robot has revolute joints and has six DOF. Individual joints are moved by DC servomotors, and their position and velocity tracked by optical encoders. The robot arm could be programmed to move into position, or manually manipulated in a passive mode. Its repeatability was measured at 0.05 mm, and error of accuracy at 2 mm. Its pneumatic gripper was used to clasp a brain retractor only. The cases were all performed with a BRW stereotactic frame in place, secured to the same rigid structure as the PUMA arm. This allows for stable transformation of stereotactic to robotic coordinates. Target coordinates were transferred to a computer work station with 3D CT images, enabling the brain retractor to be accurately placed in relation to the lesion. Progress in developing this system was limited by the inability to rapidly render updated 3D brain images in the operating room. The recent convergence of advanced computing, software and iMR imaging now allows us to initiate sophisticated neurorobotics.

A six DOF robot has also been used by Benabid from 1987 to position brain cannulae. It is attached to a stereotactic frame, and can use spatially encoded data from Xray, CT, MR imaging and angiography to plot its path. These images are also fused with digitized brain atlases to assist in surgical planning. Hundreds of stereotactic cases have been performed, including endoscopy (1–3). Similarly, URS (Universal Robotic Systems) has developed a six DOF hexapod robot called Evolution 1 for brain and spinal surgery. This system is based on a parallel actuator configuration, which provides it with high positional accuracy and large payload capacity. The positional accuracy is essential for stereotactic procedures and the high payload capacity may make Evolution 1 particularly well suited for drilling applications such as pedicle screw placements in the spine.

A simulation tool for neurosurgery, ROBO-SIM, has recently been developed. Patient imaging data is entered and the surgical target and corridor can be selected and planned. Virtual constraints are determined, creating no-go zones. The system can be connected to a robotic arm, NEUROBOT, which holds and positions an endoscope for the surgeon. NEUROBOT has four degrees of freedom if pivoted around the burr-hole. At this time, there are no published reports of it being used on patients. It is attached to a stereotactic frame, and can use spatially encoded data from Xray, CT, MR imaging and angiography to plot its path. Again, the systems have only one robotic arm and cannot emulate a human surgeon.

A dextrous robot called the Robot-Assisted Microsurgery system (RAMS), was developed by NASA's Jet Propulsion Laboratory. The mechanical subsystem is a six-DOF robot slave arm driven by tendons. This allows a large work envelope. It is designed to have 10 microns positioning accuracy. The master input device also has six tendon-driven joints. Simulated force feedback has been used, and it has potential to be used tele-robotically. RAMS is capable of being used to enhance various types of microsurgery, including ophthalmology. Although RAMS has the required dexterity, it is still a single arm system lacking the ability to reposition itself over a large worksite. It is also not MR compatible and has no direct force feedback sensing capability and is not image-guided. Patents on this development are U.S. Pat. Nos. 5,784,542; 5,710,870; 6385,509 and 6,233,504 all of Das and Ohm et al issued in 1998, 2001 and 2002.

The only MR compatible 'robot' is a simple experimental system developed by Chinzei and at the Brigham and Women's Hospital in Boston, USA. The robot consists of a passive instrument holder attached to Cartesian translational stages. The limited capabilities of the device caused it to fall into disuse.

The progress of clinical neurological sciences has depended on accurate cerebral localization and imaging technology. Over the past century, advances in cerebral imaging including contrast angiography, pneumoencephalography, and in more recent decades, ultrasound imaging, CT, MRI and frameless stereotactic navigation technology have revolutionized cerebral localization. Neurosurgery's dependence on imaging technology is epitomized by the recent flurry of iMR imaging systems developed to provide MR images during a neurosurgical procedure. Since 1996, multiple MR systems and related technologies have been developed, with over 3000 neurosurgical procedures performed worldwide. The systems possess magnet field strengths ranging from 0.12 to 1.5 Tesla, associated with varying degrees of intrusion into standard neurosurgical, anaesthetic and nursing procedures and protocols.

SUMMARY OF THE INVENTION

According to one aspect of the invention there is an provided an apparatus for use in surgical procedures comprising:

a robot for operating on a part of a patient, the robot including:
  a movable support assembly arranged to be located in fixed position adjacent a patient;
  two movable arms each carried on the support assembly;
  each arm having redundant degrees of freedom of movement;
  each arm having an end effector for carrying various surgical tools (one at a time) for operation on the patient;
  each end effector including force sensors for detecting forces applied to the tool by engagement with the part of the patient;
a microscope arranged to be located at a position for viewing the part of the patient;
and a workstation and control system including:
  a pair of hand-controllers, simultaneously manipulated by a single surgeon, each operable to control movement of a respective one of the arms;
  each hand-controller having force feedback arranged to be controlled in response to the detected forces for providing haptic feedback to the operator;
  a first display for displaying at least one image from the microscope;
  a second display for displaying on an image of the part of the patient the real-time location of the tool.

The device described in more detail hereinafter is a surgeon-operated robotic system for neurosurgery that is compatible with a Magnetic Resonance (MR) imaging system. The system allows a microsurgeon to manipulate tools tele-robotically from a control room adjacent to the operating theatre, or at a considerable distance (e.g. intercontinental and low earth orbit), and works with a specialized set of modified tools based on a subset of the standard neurosurgical tool set. The robot and tools provide 16 degrees-of freedom (DOF) movement and consists of two independently controlled surgical arms (each with eight DOF) and a camera system to view the work-site. Its function is integrated with a microscope which is placed behind the robot base, except when the robot is in stereotaxy mode and has moved down the bore of the MRI system.

The arrangement described provides a safe surgical robot that:

Has two robotic manipulators to perform surgical functions with a precision and dexterity better than the best neurosurgeon;

Is compact enough to fit and work inside an MRI magnet bore;

Is completely non-magnetic including all mechanical structures and actuators and does not interfere with MR imaging;

Allows a variety of neurosurgical tools to be used;

Achieves true image-guided surgery by registration of iMRI fiducials registered by a digitizer on the robot base, and updating this positional data with information from encoders in the robot joints. .This enhances the surgeon's situational awareness by constantly updating the position of the tool tips in relation to the surgical target.;

Provides the surgeon with a sense of feel in three DOF, that is it has haptic capability.

The robotic system has two basic modes of operation: microsurgery, and stereotactic surgery. Cranial stereotactic procedures will take place within the bore of the magnet. Microsurgical procedures will be performed outside the magnet and will involve other staff working co-operatively with the robotic system.

The use of robotics in microsurgery allows for precise motions that can be guided by microscope and/or MR images obtained during the surgical procedure, and represents a significant advance in this field. The robot will be used for parts of the procedure that require precise, tremor free motions or geometric accuracy, and as a link between the MR images and physical reality. The system consists of a Neurosurgiosi Robot, a System Controller and a Surgical Workstation. The physician controls the neurosurgical robot, located in the Operating Room, via a Surgical Workstation located in a separate Control Room. The system architecture is based on a "master-slave" control wher. the robot arm motions are slaved to the hand-controllers manipulated by the surgeon. To enhance smooth and precise motion of the surgical tool, tremor filters are incorporated and the motions of the arm may also be scaled down.

The workstation consists of the Human-Machine Interface (HMI), computer processors, and recording devices. The HMI includes two hand controllers that are used to control the spatial position and actuation of the surgical tools grasped by each arm. The surgical workstation is equipped with 4 display panels and one binocular display: one showing the 3D MR image of the brain and a real-time position of the surgical tool within the operating site; a computer status display showing system data of the robotic system; a real-time color view of the operative site captured by a field of view camera system; a 2D high resolution display of the operative field, and a 3D binocular display of the operative field. Both of the microscope displays are interfaced with high resolution cameras mounted on the right and left ocular channels of a standard surgical microscope. An additional display provides system data and control settings. The workstation contains recording devices to store intra-operative MRI and video imagery and system data. An electrical cable harness connects the robot to the System Controller. The controller translates the workstation and hand-controller commands into inputs for the robotic arm motor drives and sensors. The System Controller contains the servo-control electronics that independently move and position the robot arms. The System Controller also includes an interface for the optical joint encoders and thermistors. The backbone of the System Controller is an elaborate array of software modules and electrical hardware. The architecture of the System Controller is designed to enhance safety by single fault tolerant software and redundant electrical back-up.

The robot consists of two articulated arms with dexterous mechanical manipulators that grasp and move surgical tools attached to the arm end-effectors.

For precise tool positioning, each of the surgical arms has eight DOF. The arms are each independently small enough to operate within the confines of the working diameter of the IMRIS closed bore magnet and the device can be operated to select one or the other arm. Both can work simultaneously within an open magnet of either vertical or horizontal design. They provide frame-less stereotactic functionality when registered to fiducial markers on the head or spine. Such fiducial markers may comprise a component which can be mounted on the patient and define artifacts which can be viewed in the MR image. Such MR viewable objects are usually spherical and are made from an MR responsive material which thus generates a readily visible artifact on the MR image. Other types of optical and MR responsive objects can be used. These targets are localized and registered using a robot base-mounted mechanical digitizing arm. The images defined by the MR system can be registered relative to the arms of the robot allowing the surgeon to place the tools at the required location as determined by the MR analysis. The robot is mounted on a vertically adjustable mobile base, moved into position for the surgical procedure, and mechanically secured using locking wheels. The robot can be positioned to function as an assistant or the primary surgeon. The mobile base enables the robot to be Integrated Into any operative environment equipped with the appropriate electronic and mechanical interfaces.

Surgical tools are manually inserted into the arm end-effectors. The location and orientation of the tool tip relative to the surgical target will have an accuracy of approximately one-millimeter when relying on frameless navigation alone. Further refinement of toll tip placement is based on the surgeon assessing the stereoscopic, magnified field of view provided by the binoculars at the workstation. The final accuracy achieved is therefore only limited by the combination of the spatial resolution of our visual system (rods and cones) with 30 micron resolution that our robot has achieved on breadboard testing. The location of the tool tip can be continuously monitored using the internal arm joint angles and the virtual display of the tool acquired from iMRI.

The robot and field camera are designed to be compatible with the MR environment. Compatibility ensures that the robot produces minimal MRI artifact and conversely, the operation of the robot is not disturbed by the strong electromagnetic fields generated by the MR system. All equipment exposed to the MR field uses compatible materials, components and design practices such as:

The robot drive mechanisms use an Ultrasonic piezoelectric actuator technology.

The arms and surgical tools are made of MR-compatible materials.

All electronics are RF and magnetically shielded.

Optical force sensors /strain gauges are attached to the tool interfaces to provide force-feedback inputs. The sensors are MR compatible, immune to electromagnetic interference and possess high sensitivity and fast measurement update rates.

The workstation controls the arms by transforming commands from the hand controllers and transmitting them to the Main Controller. The hand controllers act as virtual tools for the surgeon. The motion commands are filtered to remove hand tremor and typically scaled down so, for example, a 10 cm displacement of the controller would result in a tool tip displacement of 5 mm. As a safety measure, the arms are only activated if a hand switch is depressed. This will avoid inadvertent movement of the arms caused by an accidental bumping of the hand controller. In addition to providing commands to the robot, the workstation receives feedback from the robot, the Main Controller, the MR system and other devices.

The workstation has three display types: Video, MRI and Control. The video recordings of the surgical worksite are taken by stereo cameras mounted on the surgical microscope and displayed on a high resolution 2D display and a 3D binocular display, providing the surgeon with a sense of depth. A third video display is used to show a video image of the operating room. The MRI display shows the patient's imaging data with a virtual tool position superimposed on the image. This enables the surgeon to view and track the tool in real-time, thereby facilitating image-guided surgery. The MRI can be enhanced by the administration of intravenous contrast agents to show the lesion and its relationship to adjacent structures. Lastly, the Control display is used to monitor the control systems of the robot.

Surgical simulation software on the workstation allows the surgeon to plan the point of cranial trepanation and calculate safe trajectories for the surgical corridor. Virtual 'no-go' boundaries can be defined by the surgeon, preventing inadvertent injury to neural elements. The procedure can be practiced in virtual mode by the surgeon. This will be particularly useful when performing a rare procedure, as well as in helping to teach trainee neurosurgeons.

The following sections outline the systems, electro-mechanical, and workstation components and specifications.

System Description

The workstation consists of the crucial Human-Machine Interface (HMI), computer processors, and recording devices. The HMI includes two hand-controllers used to control the motion and position of the surgical tools grasped by each arm. The surgeon has multiple surgical displays: one showing the 3D MR image of the brain and a real-time position of the surgical tool within the operating site, and the other a real-time color view of the surgical site captured by the surgical microscope. A third display will provide system data and control settings. The workstation contains recording devices to store intra-operative video imagery and system data. An electrical cable harness connects the robot to the Main Controller. The controller translates the workstation and hand-controller commands into inputs for the robotic arm motor drives. The Main Controller contains the servo-control electronics that independently move and position the robot arms. The Main Controller also includes an interface for the optical joint encoders and thermistors. The backbone of the Main Controller is an elaborate array of software modules and electrical hardware. The architecture of the Main Controller is designed to enhance safety by single fault tolerant software and redundant electrical back-up.

Electro—Mechanical Components

The robot is configured as a yaw plane manipulator to reduce the number of joints affected by gravity. It consists of two articulated arms with dexterous mechanical manipulators that grasp and move surgical tools attached to the arm end-effectors. A vision system consisting of an MR compatible camera system and white LED lights is mounted on the base and manually adjusted.

For precise tool positioning, the surgical arms have 8-DOF per arm (including tool actuation). The arms are small enough to individually operate within the confines of the 68-cm working diameter of the 1.5 T magnet. The robot is mounted on a mobile base, moved into position for the surgical procedure, and mechanically secured using wheel brakes. The robot can be positioned to function as an assistant or the primary surgeon. The mobile base enables the robot to be integrated into any operative environment equipped with the appropriate electronic and mechanical interfaces.

Surgical tools are manually inserted in the arm end-effectors. For microsurgical procedures, standard tools such as forceps, needle drivers, suction, micro-scissors and dissectors are created to fit the end-effectors. The tool actuation mechanism is comprised of a mobile ring surrounding the tool handle, the vertical movement of which controls tool actuation. Circular movement of a gear mechanism generates tool rotation. Based on the end-effector configuration, a novel micro-scissor design was implemented. For stereotactic procedures, a linear drive mechanism was designed to provide accurate insertion and targeting of a cannula and introducer. Each tool is equipped with an identifier bar and color code to automatically configure software 3D models. The models are used to calculate the location and orientation of the tool tip relative to the surgical target to an accuracy of one-millimeter. This absolute accuracy is limited by the resolution of inputs from the spatially encoded MR data and also the registration method. The registration method involves calibrating the robot coordinate frame to the MR image of the patient using MR fiducials and mechanical digitizing points. The location of the tool tip is continuously monitored using a kinematic model combined with internal arm-joint angles and the virtual display of the tool acquired from iMRI or other imaging modalities such as 3D ultrasound. The tool position is calibrated mechanically and checked against its position determined from updated MR images. An incremental tool tip resolution of 30 microns can be obtained.

The robot and field of view camera are designed to be compatible with the MR environment. Compatibility ensures the robot produces minimal MRI artifact and conversely, the operation of the robot is not disturbed by the strong electro-magnetic fields generated by the MR system. All equipment exposed to the MR field utilizes compatible materials and components including:

Piezoelectric motors are used for the robot drive mechanisms. They have the advantage of being non-magnetic, self-braking, MR-compatible, and able to meet the operating time specifications.

Material selection is critical for robot stiffness and MR compatibility. The upper and lower arm structural components are made of titanium and PEEK (Polyetheretherketone) respectively. Both materials have a very high resistivity, permitting placement inside the RF coil during transmission with minimal degradation of the coil quality factor. The intra-operative magnet and RF coil can accommodate titanium and PEEK in the imaging volume without significant loss of performance.

All electronics are RF and magnetically shielded and located as far from the high intensity fields as practical.

A three DOF optical force sensor system is used to provide haptic feedback to the surgeon. The design is based on the photo-elastic effect to measure strains in materials under stress. The end-effector is equipped with deformable flexures providing an interface for the surgical tools. Each flexure is positioned mutually perpendicular and contains its own optical strain sensor. This arrangement allows strains to be measured at the flexure surfaces. These strain measurements are used to calculate tool tip forces in the X, Y, Z directions, which are then sent back to the workstation hand controllers.

Surgical Workstation

The Surgical Workstation incorporates a computer processor, two hand-controllers to manipulate the robot arms, a controller for positioning the microscope and lights, three types of display, and data recorders. The interface is designed to maximize ergonomic comfort and minimize surgeon fatigue.

In addition to providing commands to the robot, the workstation receives feedback from the robot, the Main Controller, the MR system, and other devices. The type of information received includes: Video from the stereo camera viewing the surgical work site via the microscope; preoperative and iMR image data; tool position and motion data from the robot controller; force-sensing (haptic) data from each arm; diagnostic or error messages from the robot controller; simultaneous talk/listen voice communication with operative staff; and patient physiologic data.

Hand-controllers

The workstation controls the arms by transforming commands from the hand-controllers and transmitting them to the Main Controller. The hand-controllers act as virtual tools for the surgeon and have 6-Degrees-of-Freedom (DOF) with 3-DOF positional force feedback. The system has a large workspace and high force feedback fidelity. Motion commands are filtered to remove hand tremor and typically scaled down. For example, a 10-cm displacement of the controller could result in a tool tip displacement of 5 mm. As a safety measure, the arms are only activated if a hand switch is depressed. This avoids inadvertent movement of the arms caused by an accidental bumping of the hand-controller. The user interface of the hand-controller has been designed to maximize ergonomic comfort.

Visual Displays/Optics

The Video display presents a 3D stereoscopic view of the surgical site providing the surgeon with a sense of depth. Two precision aligned video cameras are fitted to the right and left ocular channels of a standard surgical microscope. Camera signals are presented on a proprietary high-resolution virtual stereomicroscope (binoculars) at the workstation. The same camera signal is displayed on a 2D—HDTV (High Definition Television) screen. The HDTV is positioned above the binoculars and serves as an alternative visual display for the surgeon and as a primary display for surgical staff and students. The binocular display was chosen over conventional 3D stereoscopic displays with polarization glasses to minimize the effects of ghosting and also to increase contrast and color depth of the image. The microscope is equipped with a support stand capable of motorized tilt of the microscope head. These mechanized features of the microscope allow the surgeon to remotely adjust the microscope head from the Surgical Workstation. Magnification and working distance can be controlled from the Workstation.

The MRI display shows a virtual tool position superimposed on the images. This enables the surgeon to view and track the tool in real-time, thereby facilitating image-guided surgery. The MRI is enhanced to show the lesion and its relationship to adjacent structures in both 2- and 3-dimensions.

The Control Panel display will show the following data:
System configuration: operational modes, calibration, hand-controller parameters
Robot status: tool angles and depth, system status messages, force sensor data
Physiological data: heart rate, blood pressure, expired pCO2, urinary output, blood loss, oxygen saturation
Operational scripts to outline the step-by-step procedures and contingencies Image Guidance, Simulation and Registration The image guidance system of robot provides the surgeon a means of navigation, target localization and collision avoidance. Surgical simulation software on the workstation allows the surgeon to plan the point of cranial trepanation and calculate safe trajectories for the surgical corridor. Virtual boundaries defined by the surgeon prevent inadvertent injury to neural elements. Simulated procedures can be practiced in virtual mode by the surgeon.

Registration of the robot is performed using a pre-operative MRI scan and MR fiducial targets that remain near the surgical field throughout the operation. The registration between the robot and the fiducials is accomplished using a compact 3-D digital coordinate measurement arm (digitizer) located on the base of the robot. The surgical assistant uses the digitizer arm to measure the coordinates of touch points on registration targets located near the surgical field. The coordinates are transmitted to the workstation, which uses the data to calculate the geometric coordinate transformation.

Safety Challenges and Solutions

It is a purely passive device and is exclusively controlled by an experienced surgeon at the workstation. An additional surgeon will also be scrubbed for microsurgical cases and will be able to manually intervene if ever needed. Audio communication between the robot operator and the OR team will be provided, and a video display of the worksite and MRI display duplicated in the OR. The robot's work envelope is tailored to a specific procedure, and suitably restricted. In addition to this, no-go zones are programmed into the proposed operation during the surgical planning phase. The software controlling the robot insists on continuous input from the surgeon, and a dead-man switch (safety interlock) also requires ongoing activation to prevent a lockdown. A user selectable limit is set via the software that will limit the amount of force that can be applied and can be effected by a current limit set at the servo level. If actuators fail, intrinsic braking will automatically freeze the robot. The actuators themselves are designed to function at low torque and force levels, reducing the risk of tissue injury. This has the added benefit of using small, light motors that enhance robot balance and dexterity. End-effector/tool motion will also be considerably slowed down when operating within a microsurgical corridor. It can perform dissection at a pace of 1 mm/sec or be accelerated to as much as 200 mm/sec when outside the work envelope and reaching out for tool changes. The transition to faster speeds will require two sequential but different electronic commands to prevent accidental speeding. The mobile iMRI also has inbuilt braking systems and moves at slow speeds as it approaches patients. Unplanned power interruption results in 'default' freezing of movements, and personnel can deliberately cut power through strategically placed emergency stop (E-Stop) buttons.

Clinical curbs also minimize patient risk. The current robot is excluded from performing skull exposure, as this would be a relatively difficult task for a robot but is efficiently accomplished by a surgeon. Similarly, burr-holes and bone-flaps are executed by surgeons.

The system provides an MR-compatible ambidextrous robotic system capable of microsurgery and stereotaxy. With additional surgical toolsets this system lends itself to other disciplines including plastic, ophthalmological and ENT surgery. The system has a uni-dexterous configuration for deployment within a magnet bore allowing updated image guidance for stereotactic procedures. This configuration provides additional range of motion within the magnet bore. Complex microsurgery, where both robotic arms are employed, is performed outside the magnet under supervision of a scrubbed surgeon. This will also facilitate safety and tool changing.

The system has been created de novo for the specific purpose of performing microsurgery and stereotaxy. This includes standard techniques such as micro-dissection, thermo-coagulation, and fine suturing. Procedures such as tumor resection and aneurysm clipping are possible. The design of the robot is inclusive and versatile however, and is ideal in other microsurgical specialties such as ophthalmology. The fine dexterity and low payload of the end-effectors precludes their use in gross manipulation of tissue and bone, as these tasks are more readily suited to humans. Other unique features include MRI-compatibility as tested at 3 T, and a mechanical navigation system. This makes the system the first truly image-guided surgical robot. It is also the only surgical robot with eight-DOF per arm (including tool actuation). Although this is significantly less than human DOF, it exceeds the six-DOF required to position a tool precisely in space and then orient it in the desired plane. Unnecessary DOF result in cumulative instability while insufficient DOF result in limited positioning of the manipulator. Surgeons performing microsurgery will instinctively eliminate redundant DOF by fixing their shoulder and elbow joints, but retain adequate dexterity in the hands and wrists to perform delicate microsurgery. The manipulators were designed to have the necessary dexterity to perform these same tasks.

The system provides the first authentic force feedback system in surgery. Coupled with an exceptional visual system, based on military optics, and auditory feedback from the surgical site, the system recreates the sound, sight and feel of conventional neurosurgery. The haptic sensibility component will also be useful for simulating rare procedures, and teaching neurosurgical residents.

BRIEF DESCRIPTION OF THE DRAWINGS

One embodiment of the invention will be described in conjunction with the accompanying drawings in which.

DETAILED DESCRIPTION

Further details of the above generally described system are shown in the attached drawings 1 through 17.

Figure 1:
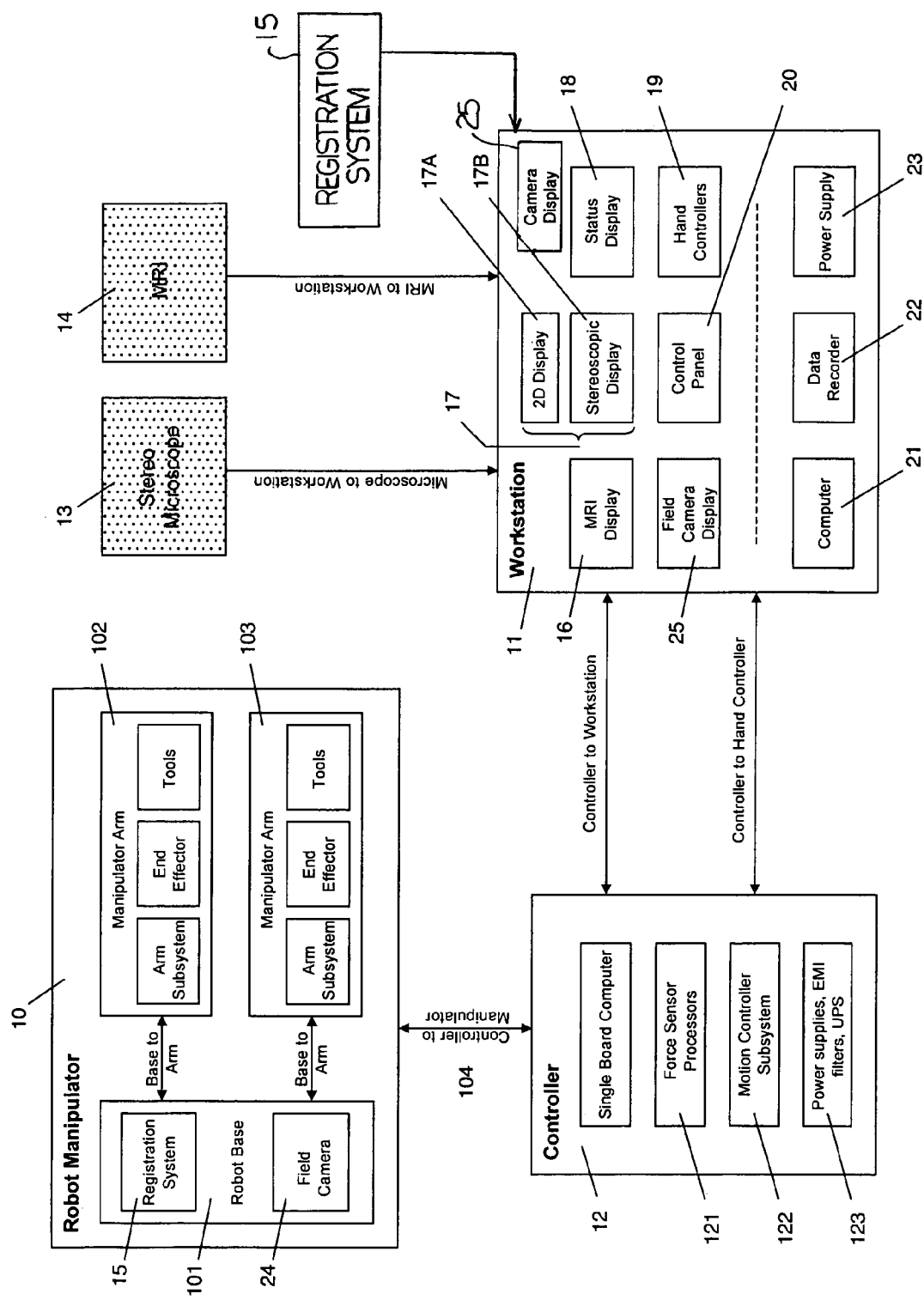
FIG. 1 is a schematic overview of the system according to the present invention.

An overview of the system is shown in FIG. 1 which comprises a robot manipulator 10, a work station 11 and a controller 12 which communicates between the robot manipulator and the work station. As inputs to the work station is also provided a stereo microscope 13, an MRI imaging system 14 and a registration system 15.

The work station includes a number of displays including at first display 16 for the MRI image, a second display 17 for the microscope image and a third display 18 for the system status. Further the work station includes two hand controllers schematically indicated at 19 and an input interface 20 allowing the surgeon to control the systems from the work station while reviewing the displays. The work station further includes a computer or processor 21, a data recording system 22 and a power supply 23.

The display 17 includes a stereoscopic display 17A which provides a simulated microscope for viewing the images generated by the stereo-microscope system 13. Further the display 17 includes a monitor 17B which displays a two dimensional screen image from the microscope system 13.

The robot manipulator 10 includes a field camera 24 which provides an image on a monitor 25 at the work station.

Figure 4:
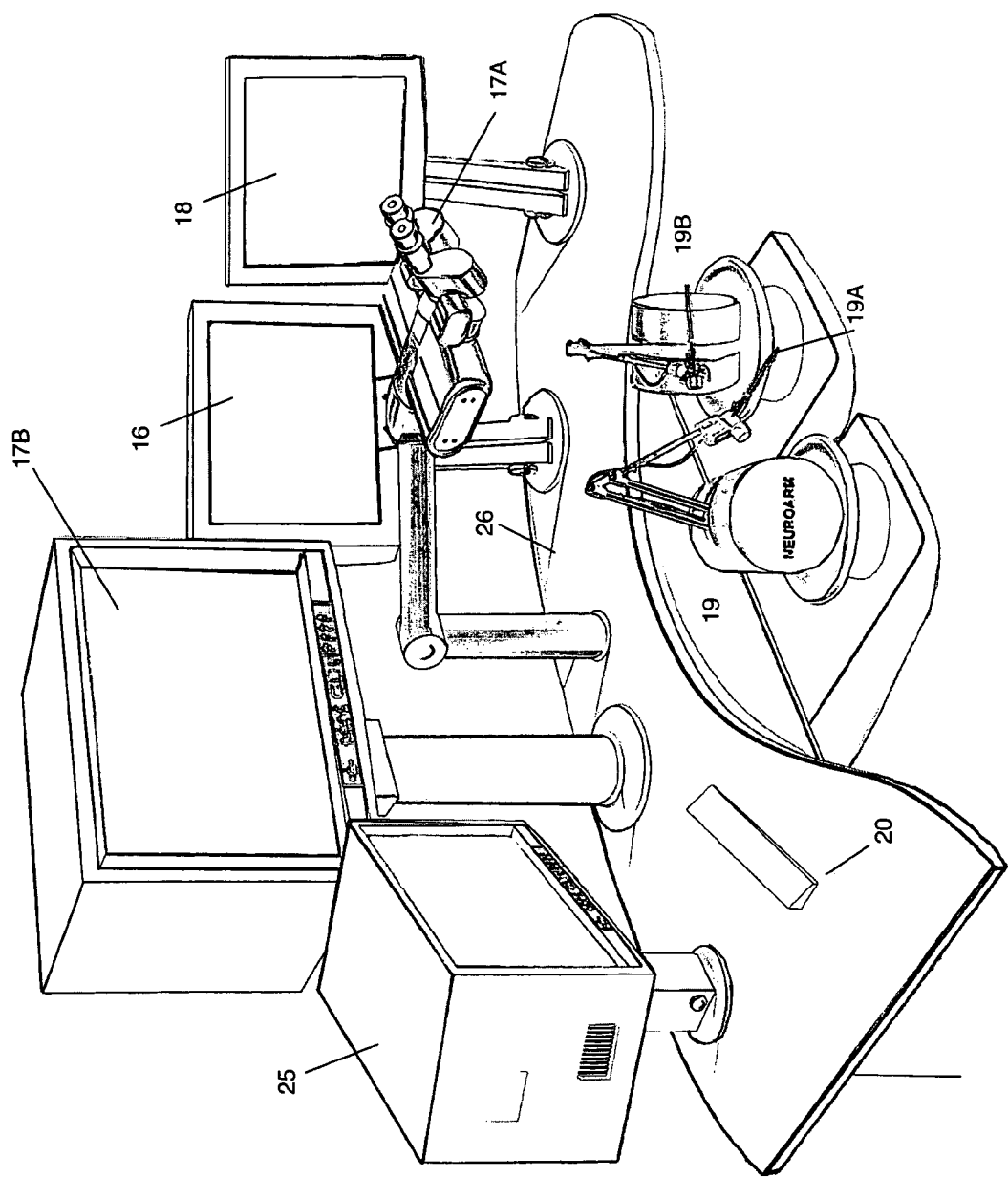
FIG. 4 is an isometric view of the workstation of the system of FIG. 1.

Turning to FIG. 4, a typical layout of the work station is illustrated which comprises a desk 26 on which is mounted four monitor screens 16, 17B, 18 and 25 together with a microscope viewing system 17A, all of which are arranged to be accessed by the surgeon seated at the desk. In front of the desk is provided the hand controllers 19 and the input terminal 20.

The stereo microscope system is of a type which is commercially available and can be mounted on a suitable support adjacent the patient for viewing the necessary site. The stereo microscope includes two separate imaging systems one for each channel which are transmitted through suitable connection to the display 17 at the work station. Thus the surgeon can view through the microscope display 17A the three dimensional image in the form of a conventional microscope and can in addition see a two dimensional image displayed on the monitor 17B.

Similarly the magnetic resonance imaging system 14 is of a conventional construction and systems are available from a number of manufacturers. The systems are of course highly complicated and include their own control systems which are not part of the present invention so that the present workstation requires only the display of the image on the monitor 16 where that image is correlated to the position of the tool as described hereinafter.

The hand controllers 19 are also of a commercially available construction available from a number of different sources and comprise 6 degrees of freedom movable arms which can be carefully manipulated by the surgeon including end shafts 19A which can be rotated by the surgeon to simulate the rotation of the tool as described hereinafter. An actuator switch 19B on the tool allows the surgeon to operate the actuation of the tool on the robot as described hereinafter.

Figure 2:
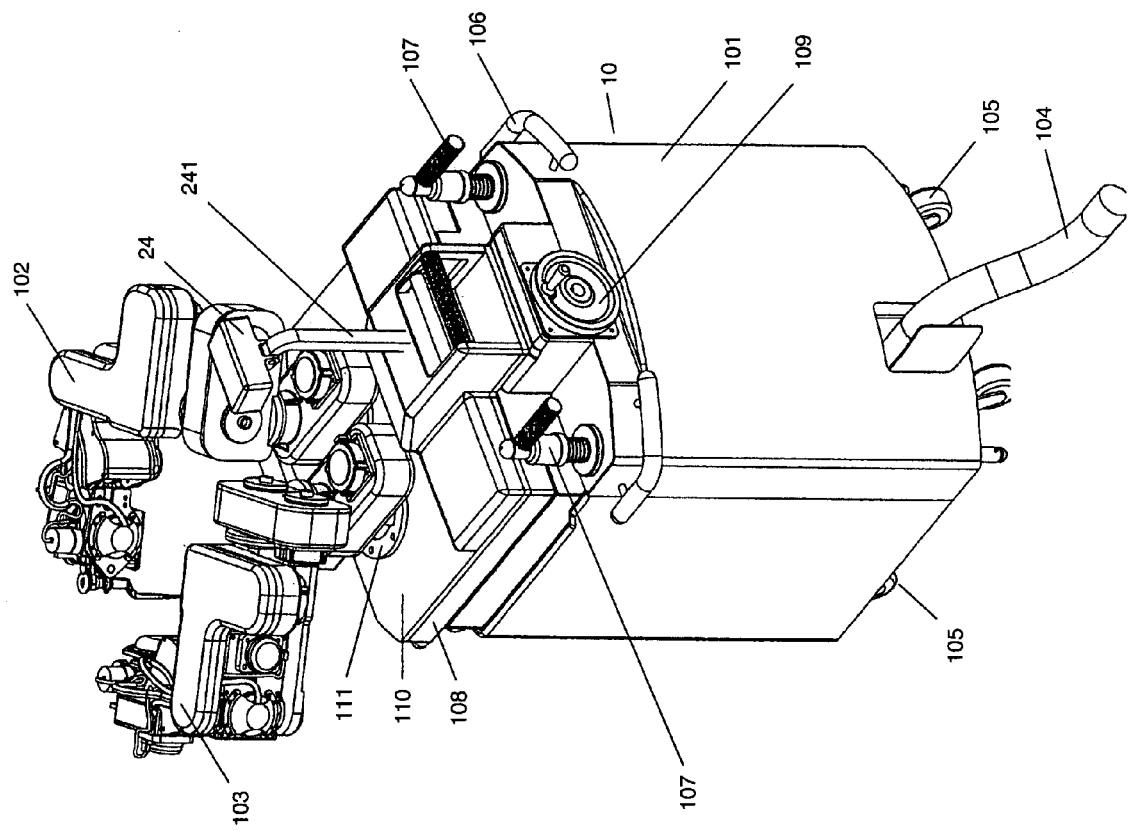
FIG. 2 is an isometric view from the rear and one side of the robot of the system according to the present invention.
Figure 3:
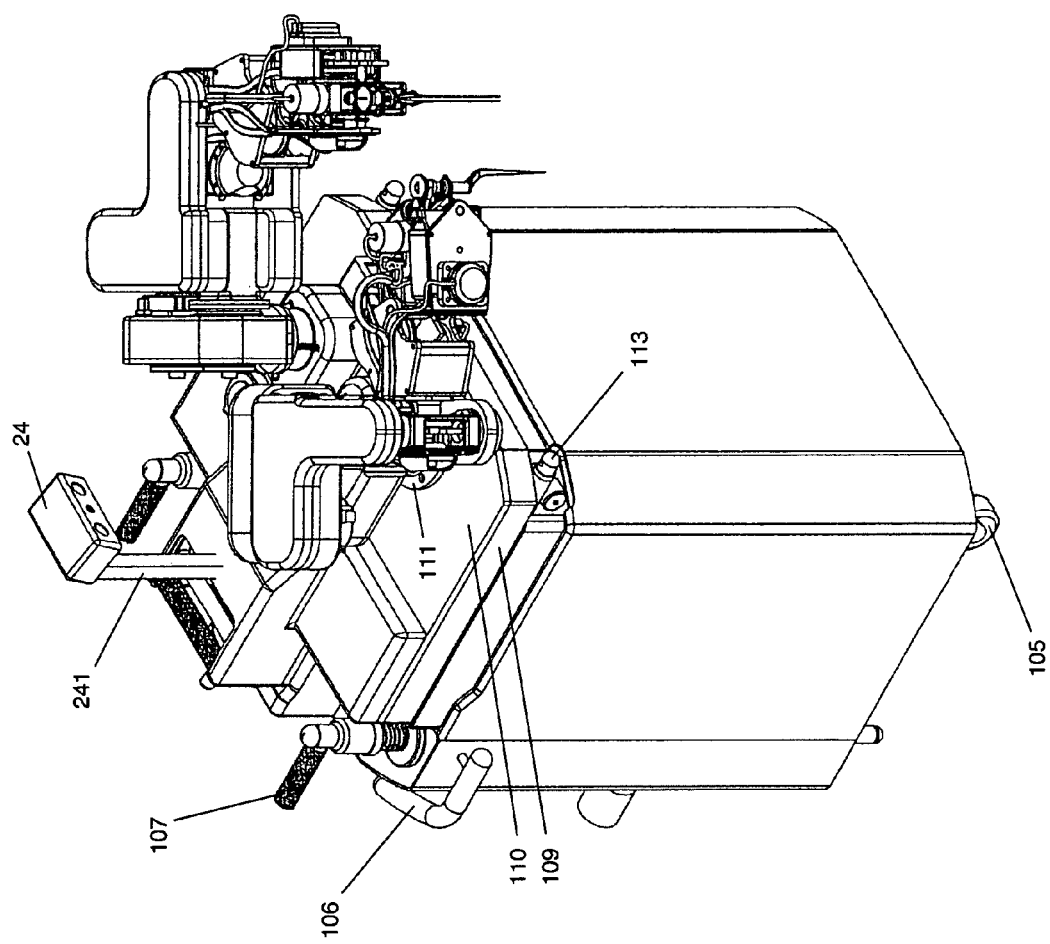
FIG. 3 is an isometric view of the robot of FIG. 2 from the front and opposite side.

The robot manipulator shown in general in FIG. 1 and shown in more detail in FIGS. 2 and 3 comprises a cabinet 101 and two arms 102 and 103 which are mounted on the cabinet together with the field camera 24 which is also located on the cabinet. The field camera is mounted at the back of the cabinet viewing past the arms of the front of the cabinet toward the patient and the site of operation to give a general overview field of the situation for viewing on the display 25.

In FIG. 1 is also shown schematically the control system for communication between the work station and the robot manipulator and for controlling the operation of each of those components. The controller includes a force sensor sub system 121 and a motion control sub system 122 together with power supplies and further components as indicated schematically at 123. The force sensor sub system controls the feed back forces as detected at the end effector of the robot arm and describes in more detail hereinafter to the hand control systems 19. The motion control subsystem 122 converts the motion control sensors from the hand-control system 19 into individual operating instructions to the various components of the arms as described in more detail hereinafter. The motion control sub system also provides an output which is communicated to the work station for display on the MRI imaging monitor 16 of the location of the tip of the tool relative to the image displayed on the screen 16, as generated by the registration system 15 as described hereinafter.

As shown in FIGS. 2 and 3, the cabinet 101 includes a communications cable 104 which connects to the controller 12. The cabinet is a mobile unit mounted on castor wheels 105 which allow the cabinet to be moved by handles 106 manually to a required location. Handles 107 act as brakes which lock the wheel and castor rotation so as to locate the cabinet 101 at a required position and maintain it fixed. The cabinet contains suitable ballast so that it is sufficiently heavy to prevent any tilting or toppling or other unintentional movements when the brakes are locked by the handles 107. The cabinet further includes a top section 108 which can be raised and lowered by a manually operable handle 109 so as to raise and lower a top mounting surface 110 which supports base plates 111 of the arms 102 and 103. Thus an operator can wheel the cabinet to the required location and can raise and lower the arms to a pre selected height so as to register with a required location for the site of the operation whether that be microsurgery on an operating table or stereotactic procedures within the bore of a magnet. The field camera 24 is mounted on a stanchion 241 so as to stand upwardly from the top portion 110 and to view forwardly across the arms 102 and 103 to the patient and the site.

Figure 5:
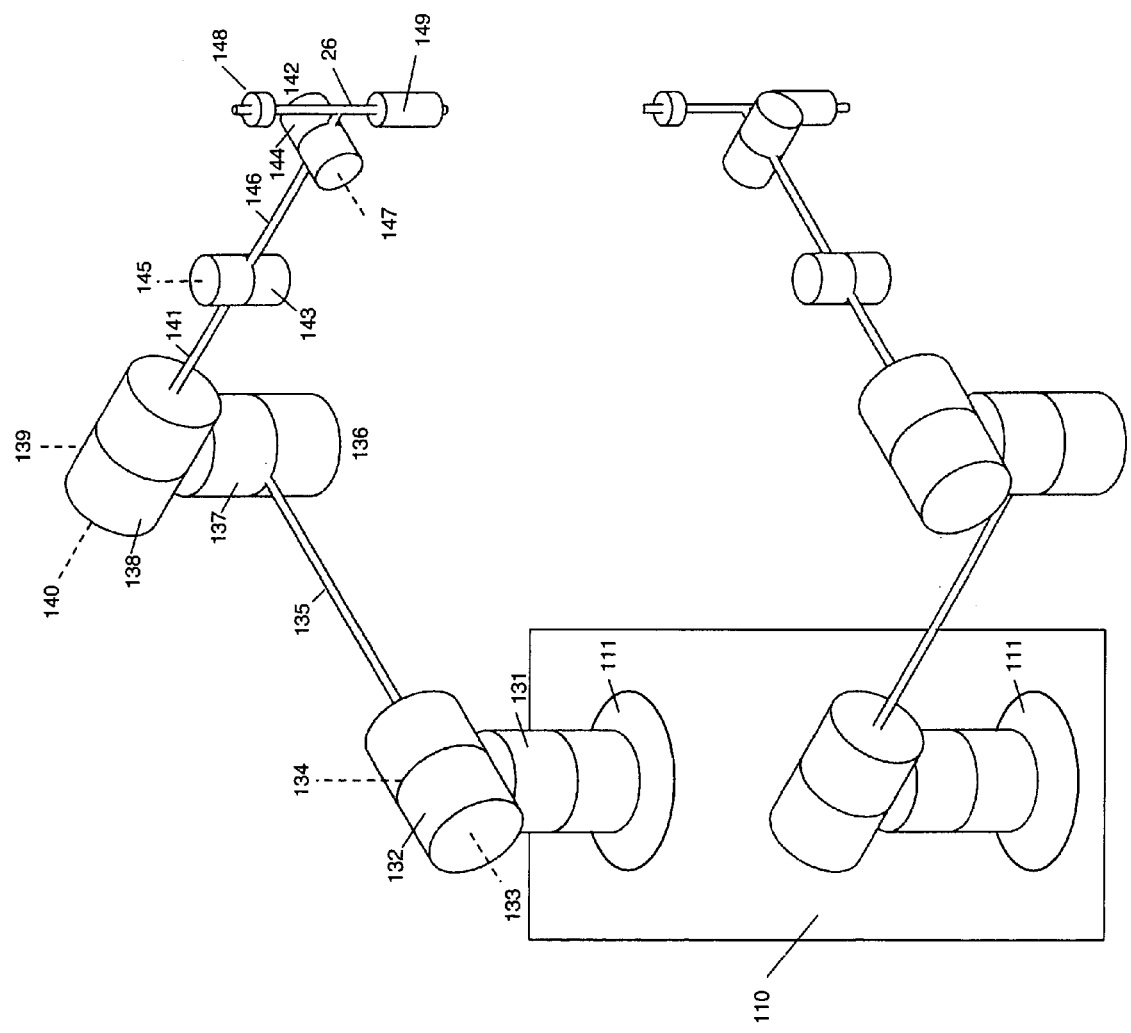
FIG. 5 is a schematic illustration of the operation of the pivots of the arms of the robot of FIG. 2.

For convenience of illustration, the structure of the arms is shown schematically in FIG. 5, where the arms are mounted with their base 111 attached to the top surface 110 and shown schematically. Each of the arms 102 and 103 includes a number of joints as shown and described hereinafter which allow operation of a tool schematically indicated at 26. Thus each arm includes a first joint defining a shoulder yaw pivot 131 defining a vertical axis of rotation. On the vertical axis is mounted a second joint 132 forming a shoulder roll joint which provides rotation around a horizontal axis 133. The shoulder yaw axis 134 extends through the joint 132. A rigid link 135 extends from the joint 132 to an elbow joint 136 which is cantilevered from the shoulder roll joint 132. The elbow joint includes an elbow yaw joint 137 and an elbow roll joint 138. The yaw joint 137 is connected to the outer end of the link 135 and provides rotation about a vertical axis 139. The roll joint 138 is located on the axis 139 and provides a horizontal axis 140. A link 141 lies on the horizontal axis 140 and extends outwardly from the joint 138 to a wrist joint generally indicated at 142. The wrist joint 142 includes a wrist yaw joint 143 and wrist roll joint 144. The wrist yaw joint 143 is located at the outer end of the link 141 and lies on the axis 140. The wrist yaw joint provides a vertical axis 145 about which a link 146 can pivot which carries the roll joint 144. The roll joint 144 provides a horizontal axis 147 which allows the tool 26 to rotate around that horizontal axis 147. The tool 26 includes a roll joint 148 which provides rotation of the tool 26 around its longitudinal axis. The tool further includes a tool actuator 149 which can move longitudinally along the tool to provide actuation of the tool as described in more detail hereinafter.

It will be noted that the axes 134, 139 and 145 are all vertical so that the weight of the supported components has no effect on the joint and there is no requirement for power input to maintain the position of the supported component to counteract its weight.

With regard to the horizontal joint 147, there is nominally a component of the weight of the tool which is applied to cause rotation around the axis 147. However the tool is located close to the axis 147 so that there is little turning moment around the axis 147 resulting in very little weight is applied onto joint 144. Thus the weight component to be rotated around the axis 147 is minimized thus minimizing the amount of force necessary to counteract the weight.

With regard to the axis 140 and the joint 138, it will be noted that the tool and the links 141 and 146 are arranged so that the center of gravity is approximately on the axis 140 thus ensuring the requirement to counteract the weight of those components since those components provide minimum moment around the axis 140.

With regard to the joint 132 and the axis 133, the weight applied to the joint 132 from the link 135 depends upon the position of the joint 137. Thus if the link 141 is aligned with the link 135 then the center of gravity of the cantilevered components from the joint 132 lie substantially on the axis 133 thus minimizing the moment around the axis 133. However it is necessary of course to operate the system that the joint 137 turn the link 141 around the axis 139 thus providing a cantilever effect to one side of the axis 133. However again this moment around the axis 133 is minimized by the selection of the system so that the arm normally operates with the center gravity of the portion of the arm outboard of the link 135 minimized.

Thus the forces required to provide rotation around the various axes is minimized and the forces required to maintain the position when stationary against gravity is minimized.

This minimization of the forces on the system allows the use of MRI compatible motors to drive rotation of one joint component relative to the other around the respective axes.

The arrangement described above allows the use of piezoelectric motors to drive the joints. Such piezoelectric motors are commercially available and utilize the reciprocation effect generated by a piezoelectric crystal to rotate by a ratchet effect a drive disc which is connected by gear coupling to the components of the joint to effect the necessary relative rotation.

Figure 5A:
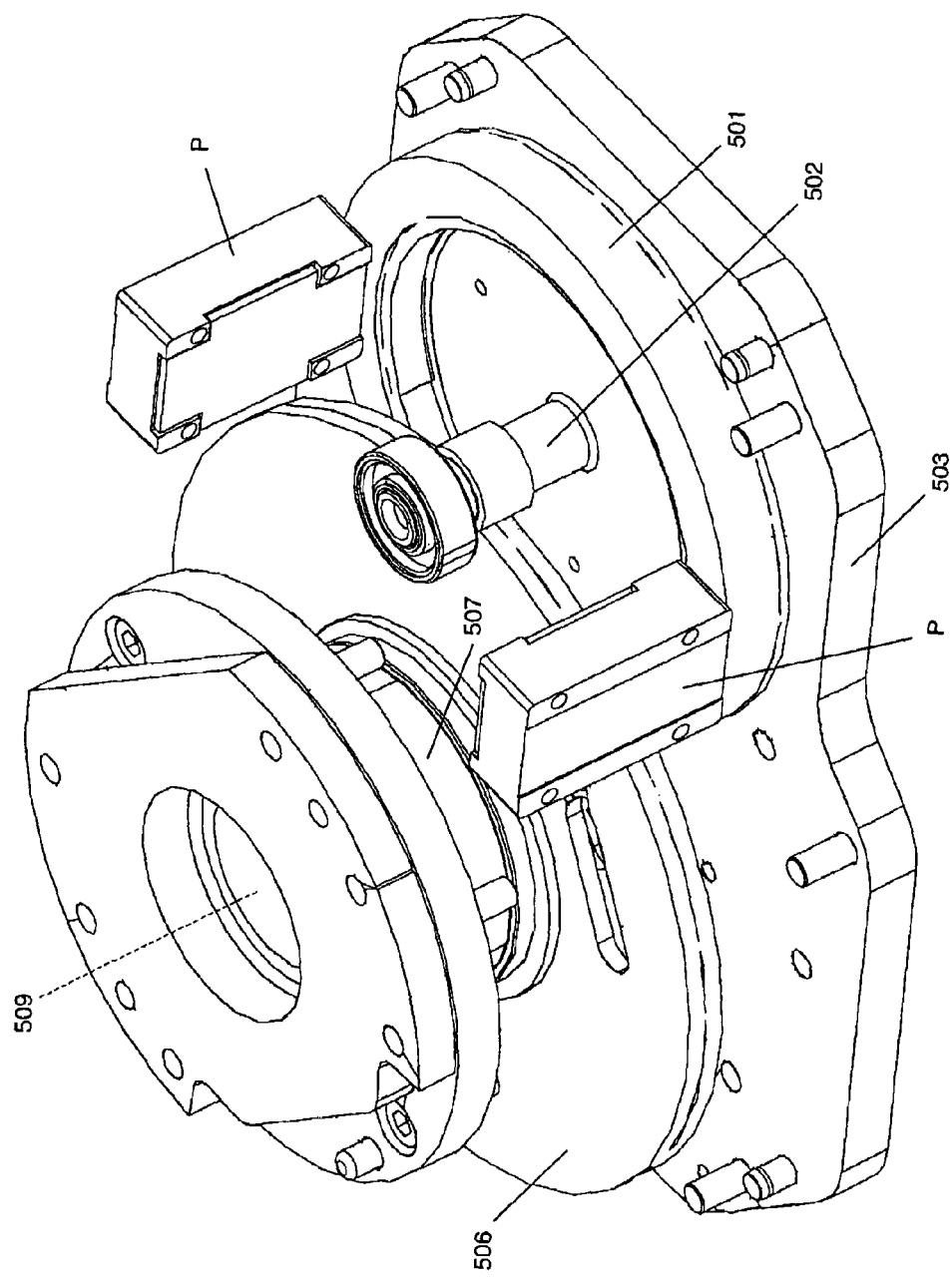
FIG. 5A is a cross-sectional view of one of the pivots of the arms of the robot of FIG. 2.

An open view of a typical joint is shown in FIG. 5A and includes two of the piezoelectric motors P driving a drive plate 501 mounted on a drive shaft 502 carried on the back plate of the housing 503 and in bearings 504 on the front plate (not shown) of the housing. The shaft 502 drives a gear 505 which is in mesh with a driven gear 506 on a driven shaft 507. The driven shaft 507 rotates one part 508 of the joint relative to the other part which is attached to the housing 503 about the joint axis 509.

The joint shown in FIG. 5A uses a dual piezoelectric motor arrangement and is thus used for the larger joints at the shoulder and elbow. For the smaller joints such as the wrist and tool actuation, the same piezoelectric motor is used but one of these motors is used to provide the necessary torque.

Figure 6:
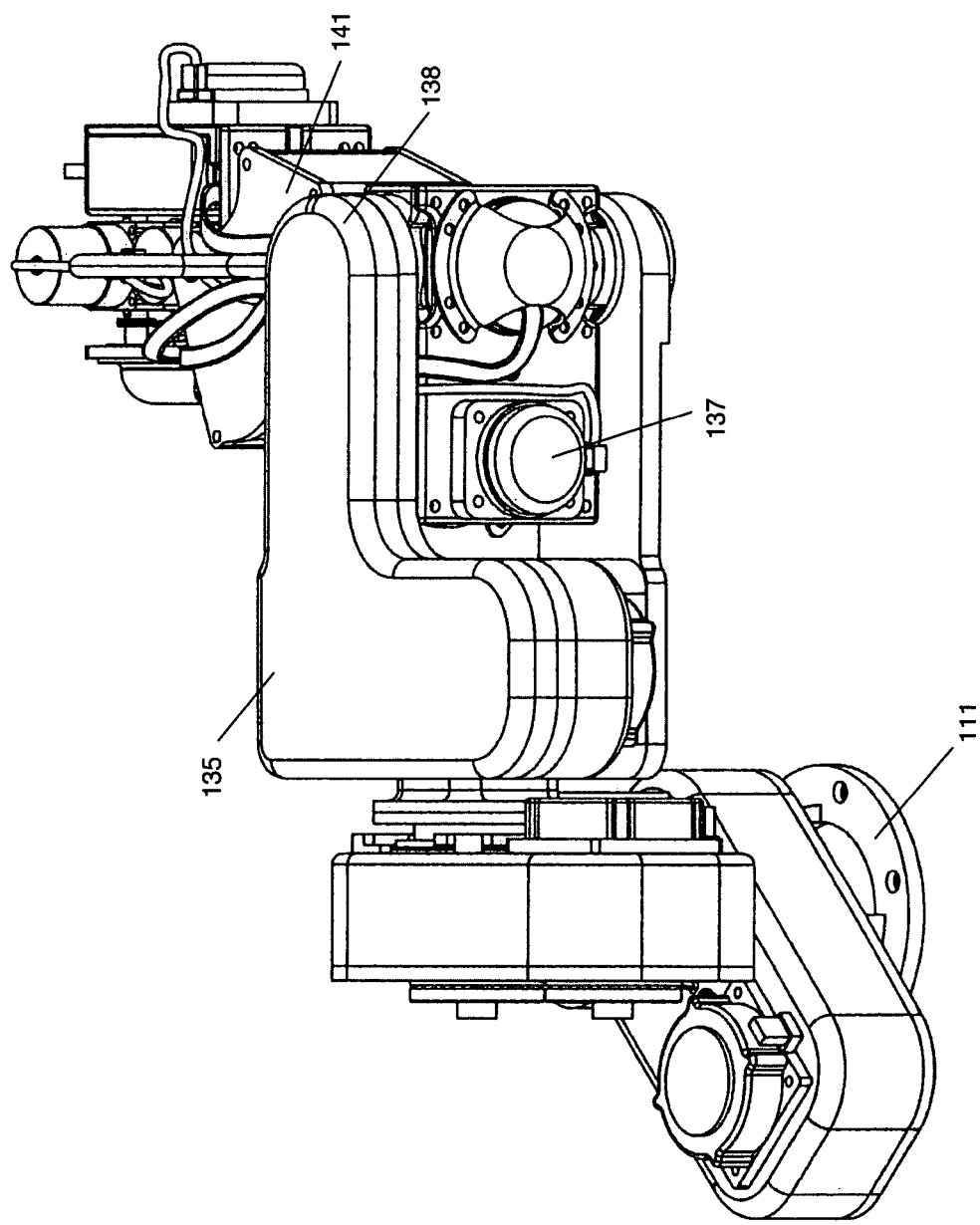
FIGS. 6 and 7 are isometric views of one arm of the robot of FIG. 2.
Figure 7:
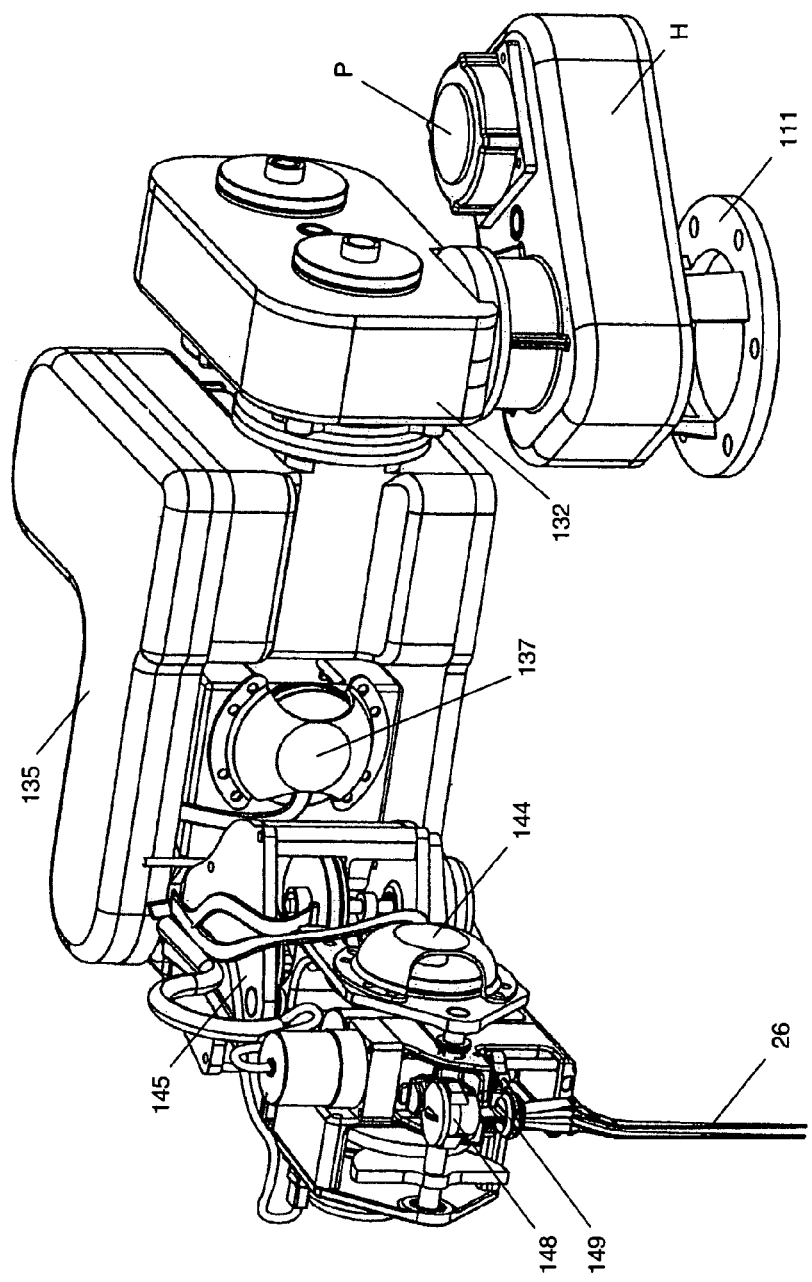

A suitable construction of the motors and links for the arms to embody the schematic arrangements shown in FIG. 5 is shown in FIGS. 6 and 7. Thus the various components are marked with the same reference numerals as set forth in FIG. 5. It will be noted that the joints are of a similar construction with each including a piezoelectric motor P mounted in a housing H. The motor P drives the joint by a gear coupling arrangement from a disc at the motor P to the rotatable portion of the joint on the respective rotation axis. Thus the axis of the motor P is offset to one side of the axis of rotation of the respective joint and provides the required controlled rotation determined by the rotation of the drive disc of the piezoelectric motor. Dual optical encoders shown as 137 are used at each joint to measure joint angle position. The dual arrangement provides redundancy. The encoder is used to determine whether the required movement has been obtained.

Figure 8:
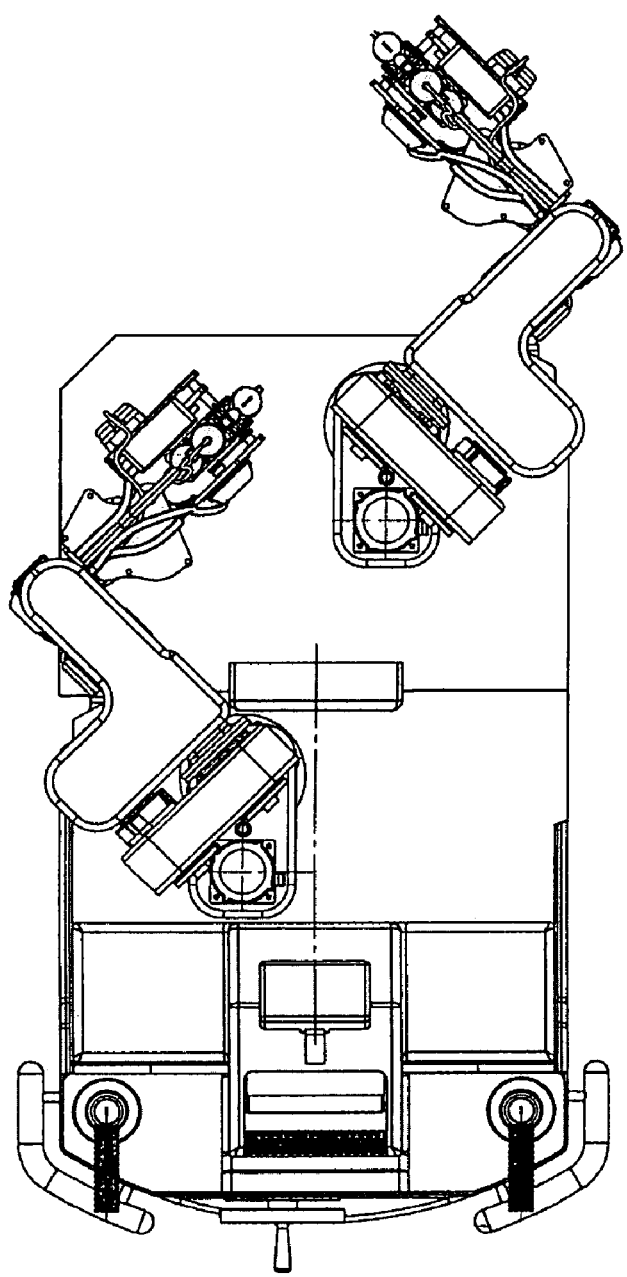
FIG. 8 is a top plan view of the robot of FIG. 1 showing one arm advanced for insertion into a magnet bore of an MRI imaging system and the other arm retracted to allow engagement of the cabinet with the bore.
Figure 9:
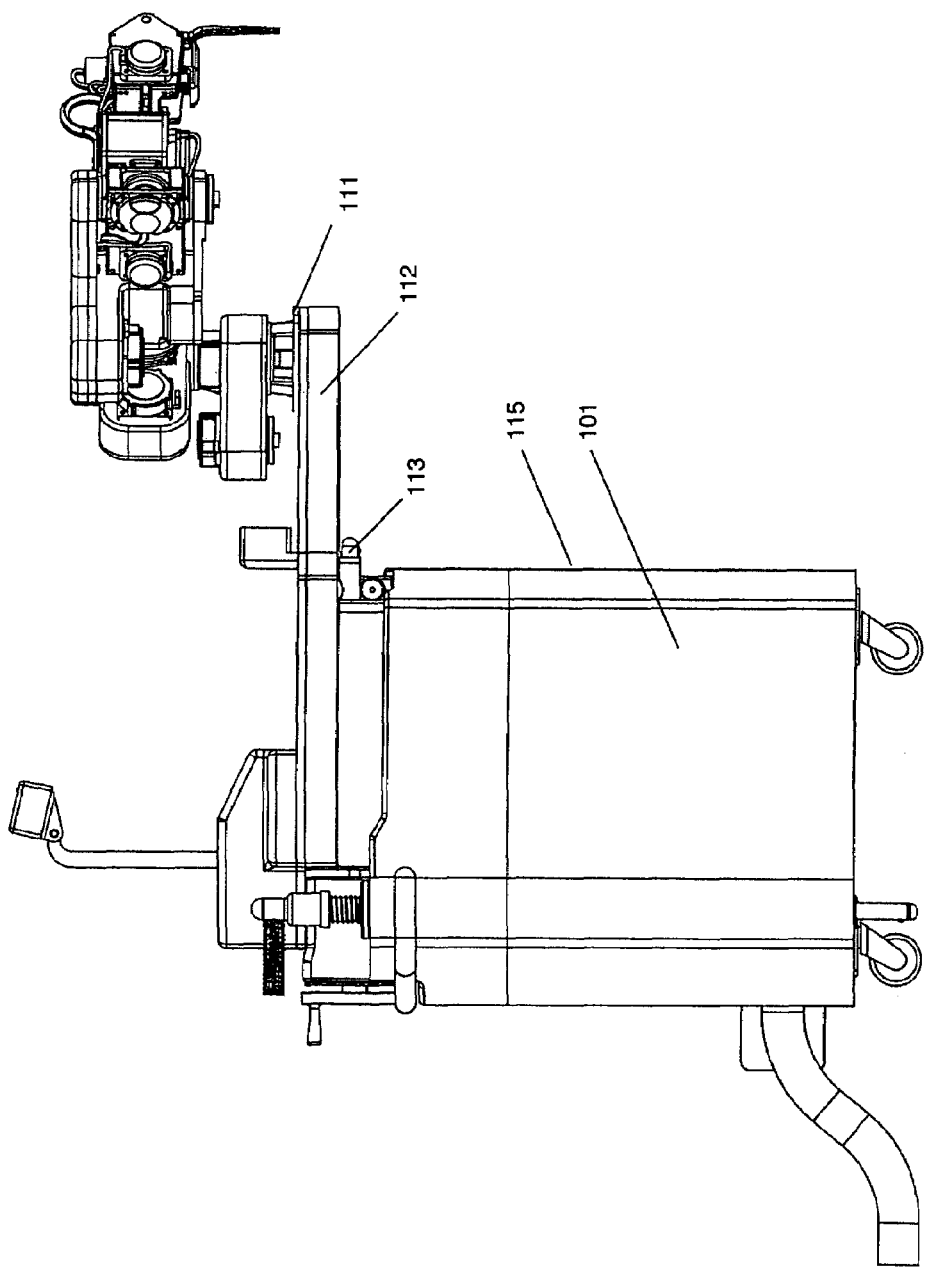
FIG. 9 is a side elevational view of the robot in the configuration of FIG. 8.

Turning now to FIGS. 8 and 9, it will be noted that the construction has been operated to move the arms from the double arm operating system to a single arm operating system for use in co-operation with the bore of a closed bore magnet. Thus in FIGS. 8 and 9, an additional table portion 112 is mounted on the front of the cabinet 101 on mounting pins 113. This allows a selected one of the arms 102 and 103 to be moved with its base plate 111 sliding along a track 114 on the table top 112 to a position advanced in front of a front wall 115 of the base cabinet 101. At the same time the other of the arms is turned to a retracted position so that it is wholly behind the front wall 115 as best shown in FIG. 8. Either of the arms can be selected for movement in a respective track to the forward position since the arms have different work envelopes within which they can move so that, depending upon the location of the site in which operation is to take place, one or other of the arms provides a better field of operation and thus should be selected. The remaining arm remains in place on the table top 110 and is suitable retracted to avoid interference with the opening of the magnet bore.

The robot therefore can be used in the two arm arrangement for microsurgery in an unrestricted area outside of the closed bore magnet or for microsurgery within an open bore of a magnet should the arrangement of the magnet be suitable to provide the field of operation necessary for the two arms to operate. The two arms therefore can be used with separate tools to effect surgical procedures as described above.

Within the bore of a closed magnet, there is insufficient room to receive both arms of the device so that the single arm can be used to effect stereotactic procedures. Such procedures include the insertion of a probe or cannula into a required location within the brain of the patient using the real time magnetic resonance images to direct the location and direction of the tool. Thus the single arm system can be used to carry out whatever procedures are possible with the single arm but procedures requiring two arms must be carried out by removing the patient from the closed bore moving the patient to a required location where sufficient field of operation is available, restoring the robot to its two arm configuration with the table top 112 removed and locating the robot at the required position relative to the patient and the operating table.

Figure 10:
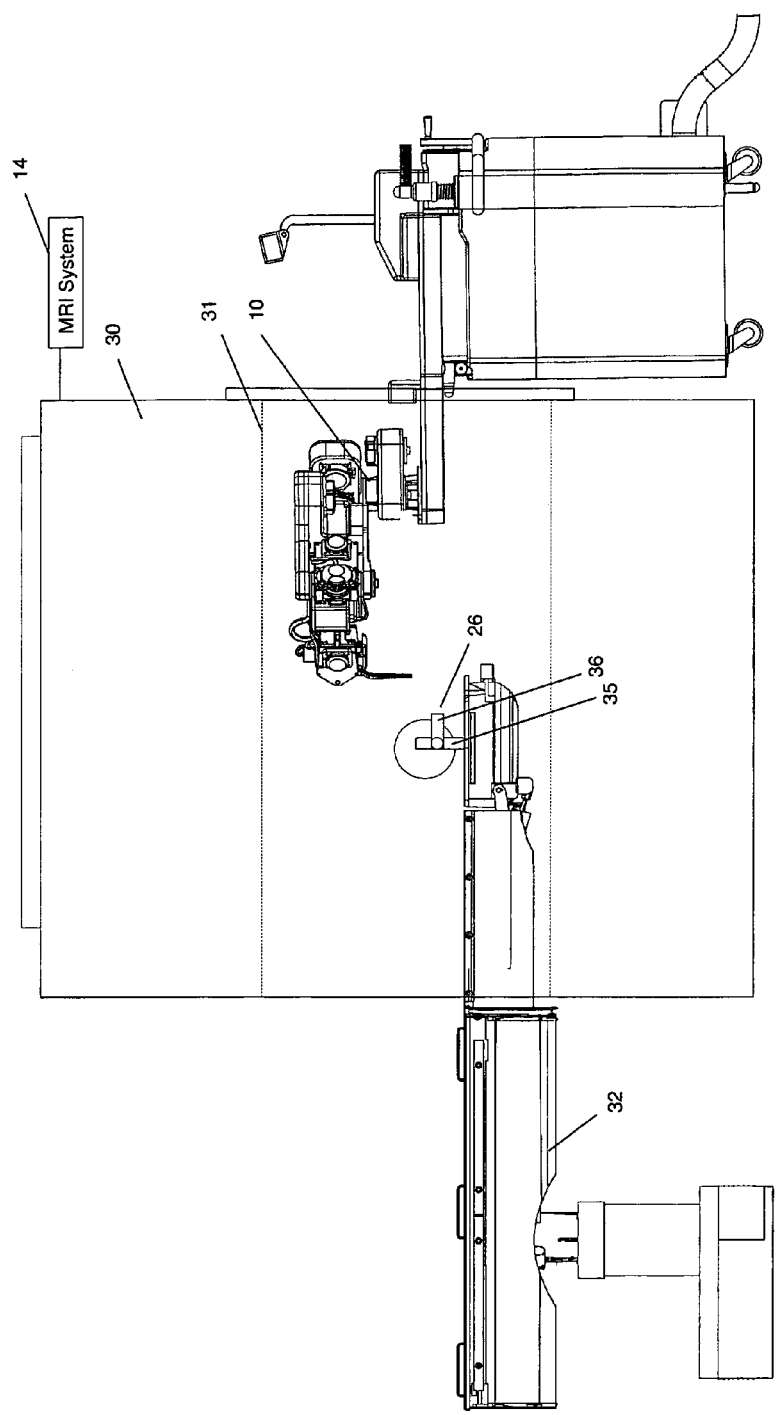
FIG. 10 is side elevational view of the robot in the configuration of FIG. 8 in conjunction with a patient table and the MRI magnet.

In FIG. 10, the system is shown schematically in operation within the bore of a magnet 30 of the MRI system 14. The bore 31 is relatively small allowing a commercially available patient table 32 to carry the required portion of the patient into the bore to the required location within the bore. The field camera is used within the bore for observing the operation of the robot 10 and particularly the tool 26.

The registration system 15 includes a mount 35 fixed to the head of the patient and including fiducial markers 36 carried on the mount. The mount is of a conventional head clamp construction commercially available. The fiducial markers are small objects which are located at fixed positions around the head of the patient in a predetermined configuration or array which can be located by the registration system so as to properly orient the registration system relative to the image generated by the MRI system 14. Thus the fiducial markers are formed of a material which is visible on the MR image so that the markers can be seen in the image as displayed on the monitor 16.

The same fiducial markers can be used in the MRI system even when the robot is not used in the MRI system for carrying out any procedures so that the image generated on the MRI system is registered relative to the fiducial markers or points located on the head of the patient.

Figure 11:
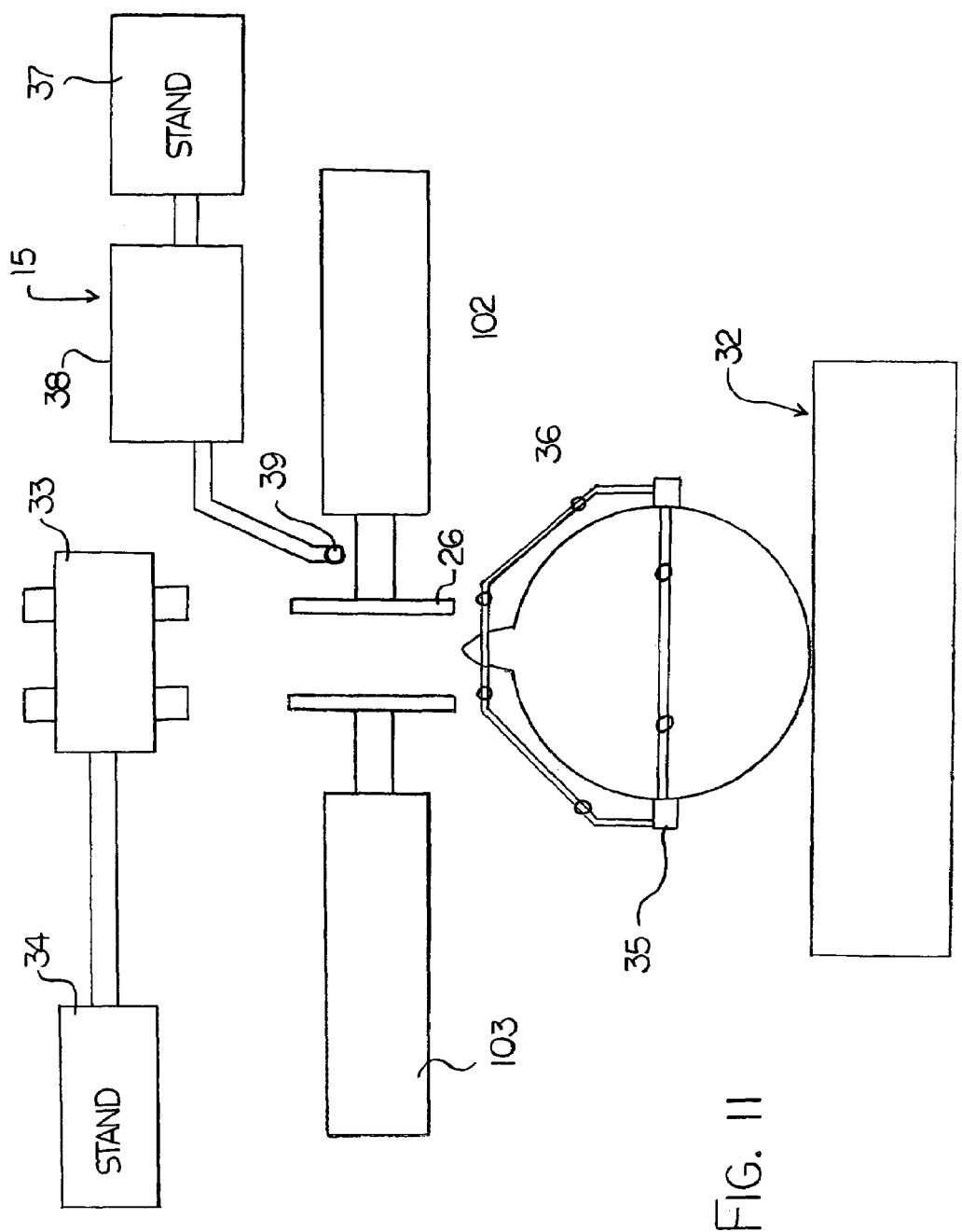
FIGS. 11 is an end elevational view of a patient operating table and including the robot in co-operation with the microscope and location registration system.

As shown in FIG. 11, the patient on the table 32 is moved to the operating position which is accessible by the arms 102 and 103 and the tools 26 carried thereby. The patient carries the head restraint 35 which is fixed in the same position relative to the head of the patient as it was during the MRI process including the fiducial markers 36.

At the operating position on the table 32 is located the microscope 33 on the stand 34 which is moved to position the microscope to view the operating site at the operating location on the table 32.

The registration system 15 includes a stand 37 carrying a registration probe and associated control system 38 with the probe including a probe tip 39. The registration system 38 is mounted at a fixed position so that the location of the probe tip 39 in X, Y and Z co-ordinates can be located and determined by the registration system for communication to the robot control 12.

Thus, with the patient fixed in place by the clamp 35, the position of each of the fiducial markers 36 is identified by the tip 39 thus providing to the system the co-ordinates of that fiducial marker. In addition the instantaneous position of the tip of the tool 26 is input into the same system thus registering the tool tip relative to the fiducial markers and therefore relative to the image displayed on the monitor 16.

The system is therefore operated so that the control unit 12 operates to move the tool tip to a required position and at the same time indicates to the display system the actual location of the tool tip in the registered space defined by the fiducial markers and displayed on the monitor 16. The surgeon is therefore able to view the location of the tool tip on the monitor 16 relative to the previously obtained image and maintain the registration of those images.

In procedures carried out during the MR imaging process, the tool tip can be formed in manner which allows it to be visible in the image so that the surgeon obtains a real time image from the MRI system which locates the tool tip relative to the volume of interest visible on the monitor displaying the image.

The end effector is shown in FIGS. 12 through 17. The tool 26 is mounted on its upper end in the role actuator 148 so as to extend downwardly therefrom to the tip 40. The upper end of the tool is supported while allowing some side to side and front to back movement of the tool relative to the actuator 148. This movement is constrained by a collar at the actuator 149 which surrounds the tool and holds the tool along the axis of the actuator 148.

The tool support mechanism 148 allows rotation around the longitudinal axis 42 of the tool by a drive gear 42 actuated by a further motor P. Thus the tool, while held on the axis 42 can be rotated around its length to move the tip 40 of the tool around the axis.

Actuation of the tool is effected by moving the actuator 149 longitudinally of the axis 42. For this purpose the actuator 149 is mounted on a slide 43 carried in a track 44 and driven by a suitable mechanism along the track 44 so as to accurately locate the position of the actuator 149 along the length of the tool.

Figure 12:
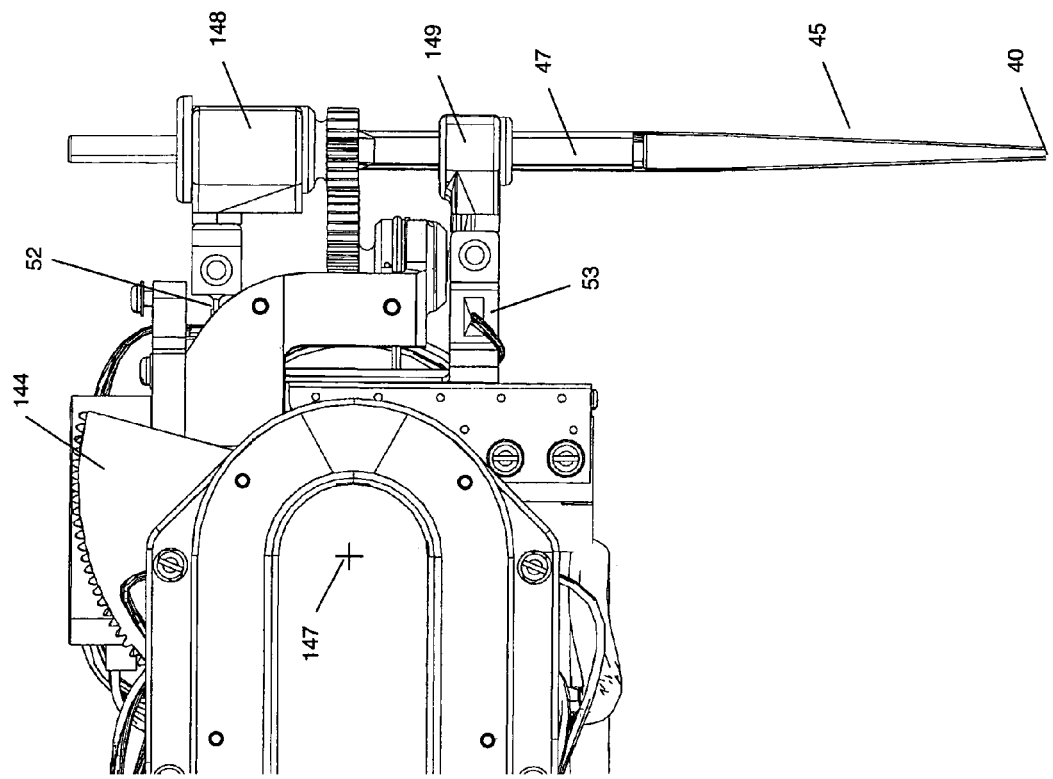
FIG. 12 is an enlarged side elevational view of the end effector including a pair of forceps mounted in the end effector.
Figure 13:
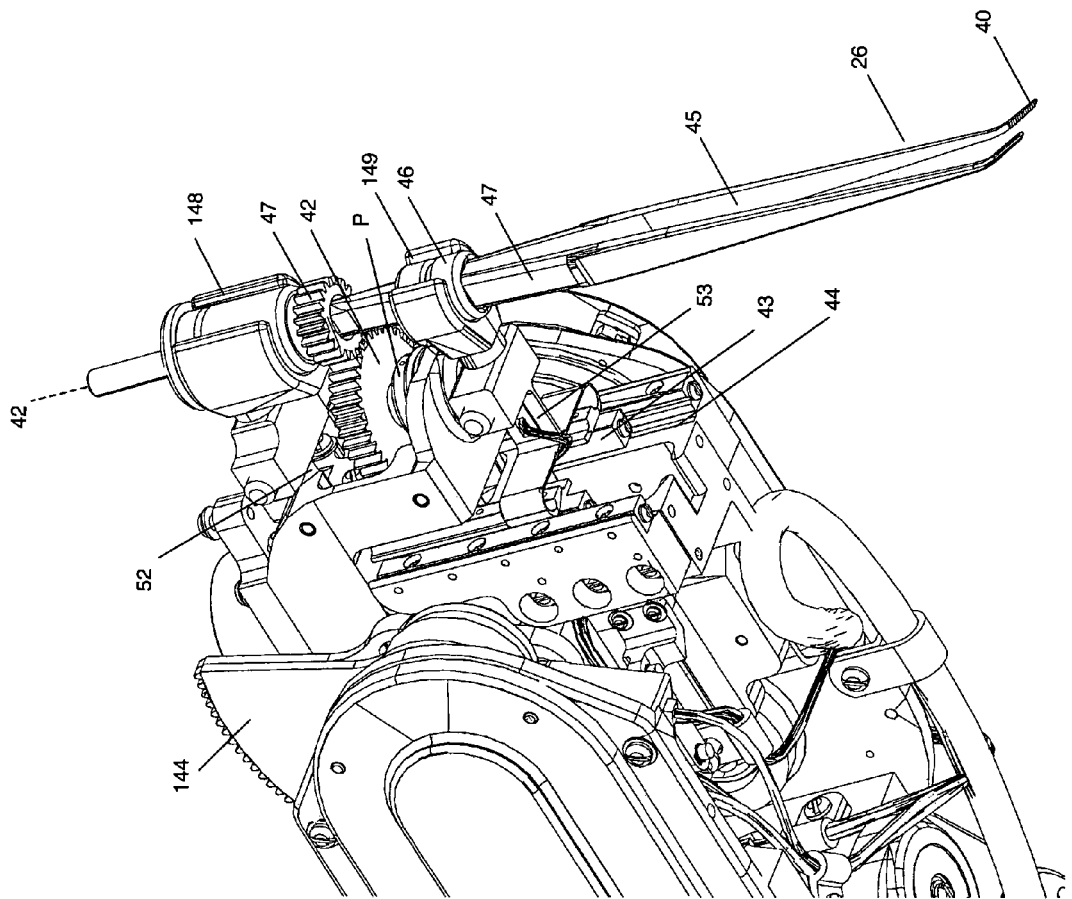
FIG. 13 is an enlarged isometric view of the end effector of FIG. 12.

In the example shown in FIGS. 12 and 13, the tool comprises forceps 45 which are actuated by moving the ring 46 of the actuator 149 along ramp surfaces 47 on the sides of the blades of the forceps 45. Thus the position axially of the ring 46 along the ramp surfaces 47 determines the spacing of the tips of the forceps.

Detection of the forces is applied on the tip 40 by an object engaged by the tip 40 is effected by top and bottom flexure detection components 52 and 53. Thus the actuator 148 is mounted on the top flexure component which is arranged to detect forces along the axis 42. The bottom flexure component is attached to the actuator 49 and is used to detect side to side and front to back forces in the X, Y plane.

Suitable flexure detection components are commercially available and different types can be used. For use in the magnet, however, the detection components must be MRI compatible.

One suitable example of a flexure detection system is that which uses a known optical detection system. Thus the flexure component includes a member which is flexed in response to the forces and the flexure of which changes the characteristics of reflected light within the member. Fiber optic cables supply a light source and receive the light component from the reflection, communicating the reflected light through the arm to a control module within the cabinet of the robot. Thus forces flexing the member in response to engagement of the tip of the tool with an object are communicated to the control module within the cabinet which converts the reflected light to an electrical signal proportional to the forces applied.

The control module in the cabinet communicates the electrical signals proportional to the forces to the control unit 12 of the system. These forces are then amplified using conventional amplification systems and applied to the hand controllers so as to provide the previously described haptic effect to the surgeon at the hand controllers.

Figure 14:
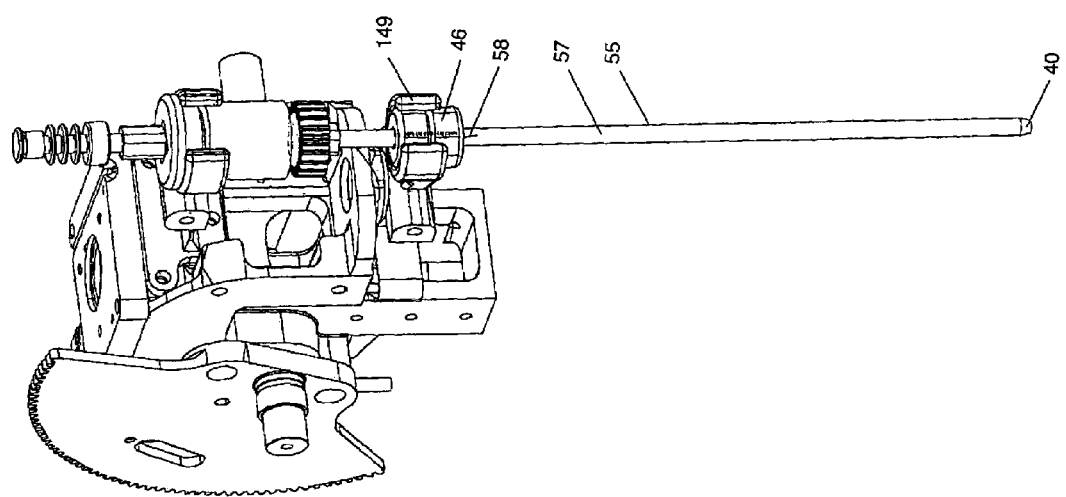
FIGS. 14, 15, 16 and 17 are isometric views of the main components of the end effector of FIG. 12 including four different tools, specifically a suction tool, a micro-dissection tool, micro-scissors and bipolar forceps respectively.

In FIG. 14 is shown a suction tool 55 which is used in replacement for the forceps shown in FIG. 13. Thus the forceps are removed by sliding the tool 26 longitudinally out of its engagement with the upper roll actuator 148. Thus the tool is removed from the collar 46 of the lower actuator 149. The suction tool 55 includes a connection 56 to a source of suction for applying a suction effect at the tip 40 of the suction tool. The amount of suction applied at the tip 40 relative to the suction source is controlled by moving the actuator ring 46 longitudinally of the tube 57 forming the tool. The tube 57 includes an inlet opening at the ring 46 which is partially or wholly covered by the ring 46. Thus when the opening 58 is fully exposed as shown in FIG. 14, the suction effect is minimized or removed so that little or no suction is applied at the tip 40. Partial covering of the hole 58 increases the suction effect up to a maximum when the hole is fully covered by the ring 46.

Figure 15:
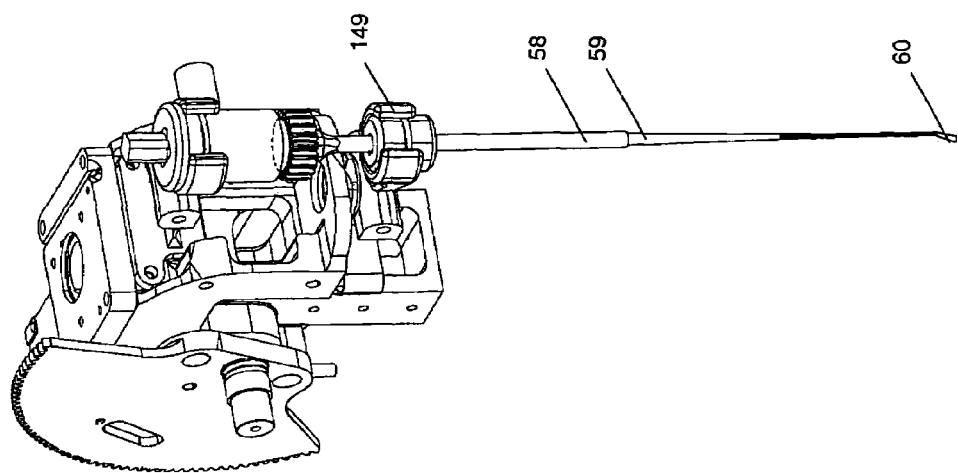

In FIG. 15 is shown a micro dissection tool 58 which is mounted as previously described. This tool simply comprises an elongated tool bar 59 with a tip 60 shaped for various well known functions which are available to the micro surgeon. As previously described, the tip can be rotated to a required orientation around the axis of the tool bar. In this tool, the lower actuator 149 is not operated but is merely used to detect side to side and front to rear forces as previously described.

Figure 16:
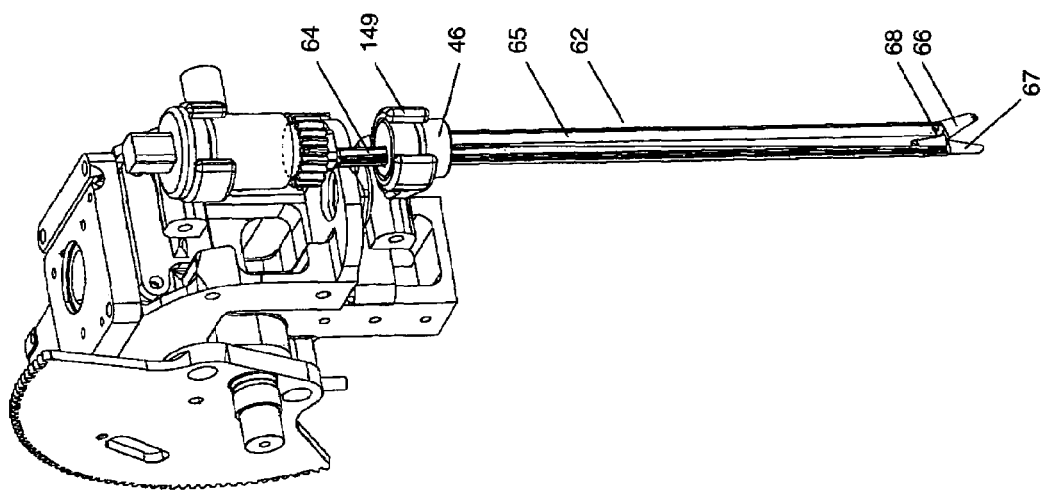
Figure 17:
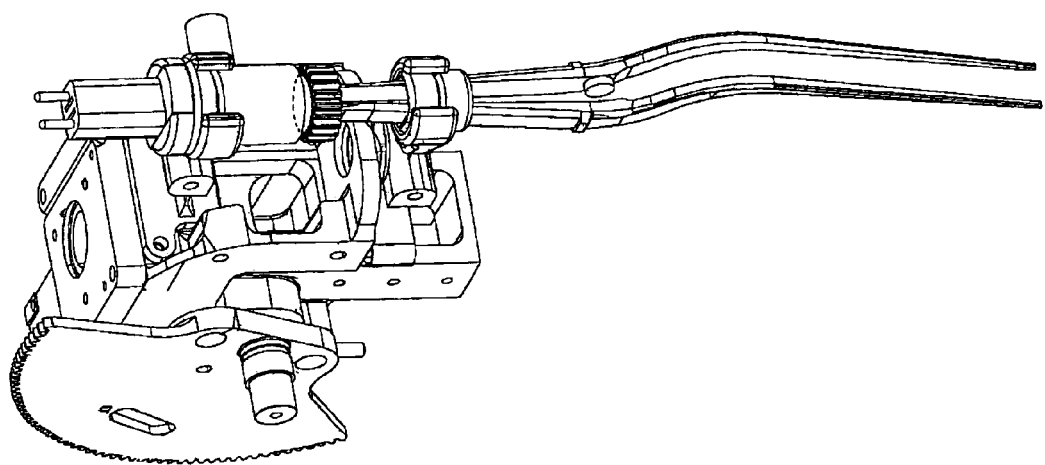

In FIG. 16 is shown a micro scissors tool 62 which is mounted in the upper and lower actuators as previously described. The scissors include a tool bar 63 which is held at its upper end 64 by the upper actuator, together with an actuator rod 65 which is carried by the lower actuator 149. Upward and downward movement of the rod 65 actuates one blade 66 of a pair of scissors blades 66 and 67 in a cutting action by pivoting the blade 66 about a suitable support pivot 68.

The invention claimed is:

1. Apparatus for use in micro-surgery and stereotactic surgical procedures on a patient comprising:
    an imaging system for obtaining a three dimensional internal image through a selected part of the body of the patient;
    a robot for operating on a part of a patient, the robot including:
    a movable support assembly arranged to be located in fixed position adjacent a patient;
    two movable arms each carried on the support assembly;
    each arm having a plurality of degrees of freedom of movement;
    each arm having an end effector for carrying a selected surgical tool for operation on the patient;
    each end effector including force sensors for detecting forces applied to the tool by engagement with the part of the patient;
    a microscope arranged to be located at a position for viewing the part of the patient;
    and a workstation and control system including:
    a pair of hand-controller simultaneously manipulated by an operator to control movement of a respective one or both of the arms;
    each hand-controller having force feedback arranged to be controlled in response to the detected forces for providing haptic effect to the operator such that the hand-controllers can control the arms in effecting microsurgery;
    a first display for displaying at least one first image obtained from the microscope;
    a second display for displaying a second image obtained from the imaging system of the part of the patient and for displaying on the second image the real-time location of the tool such that the tool can be guided in stereotaxy.

2. The apparatus according to claim 1 wherein there is provided on the robot a field camera operable for generating a field image of the part of the patient.

3. The apparatus according to claim 1 wherein the imaging system for generating the second image is an MRI system and wherein the tool is arranged to be visible in the MRI system such that the image of the tool is visible on the second image of the patient.

4. The apparatus according to claim 1 wherein each arm has joints defining six degrees-of-freedom and the end effector for the tool actuation has two degrees of freedom.

5. The apparatus according to claim 1 wherein the end-effector includes a roll actuator for causing roll movements of the tool about a longitudinal axis of the tool and a tool actuator for causing actuation movements of the tool.

6. The apparatus according to claim 5 wherein the tool actuator is a linear drive mechanism designed to effect movement of an actuation member along the tool.

7. The apparatus according to claim 6 wherein the linear drive mechanism provides accurate movement and targeting of a cannula and introducer for MR guided stereotactic procedures.

8. The apparatus according to claim 5 wherein the tool actuator is a linear drive mechanism designed to effect movement of an actuation member along the tool, wherein the tool comprises a pair of forceps and wherein the actuation member comprises a collar for engaging ramp surfaces on the forceps for actuating a squeeze movement of the forceps.

9. The apparatus according to claim 5 wherein the tool actuator is a linear drive mechanism designed to effect movement of an actuation member along the tool, wherein the tool comprises a pair of scissors and wherein the actuation member moves an actuating rod longitudinally of the scissors for pivoting one blade of the scissors.

10. The apparatus according to claim 5 wherein the tool actuator is a linear drive mechanism designed to effect movement of an actuation member along the tool, wherein the tool comprises a suction duct and wherein the actuation member moves a blocking collar longitudinally of the suction duct for exposing or covering a suction release opening of the suction duct.

11. The apparatus according to claim 1 wherein the robot includes a dead-man switch in the robot hand controllers to prevent inadvertent movement of the robot arm and alternative dead-man switches located on the workstation and the robot base.

12. Apparatus for use in surgical procedures on a patient comprising:
   an imaging system for obtaining a three dimensional internal image through a selected part of the body of the patient;
   a robot for operating on the part of the body of the patient, the robot including:
   a movable support assembly arranged to be located in fixed position adjacent the patient;
   at least one movable arm carried on the support assembly;
   said at least one arm having a plurality of degrees of freedom of movement;
   said at least one arm having an end effector for carrying selected surgical tool for operation on the patient;
   at least one camera arranged to be located at a position for obtaining a visual image of the part of the patient;
   and a workstation and control system including:
   at least one hand-controllers to be manipulated by an operator to control movement of said at least one arm;
   a first display for displaying the visual image obtained from the at least one camera;
   a second display for displaying the three dimensional internal image obtained from an imaging system of the part of the patient and for displaying on the three dimensional internal image the real-time location of the surgical tool;
   wherein there is provided a registration system including fiducial marker members located at the part of the patient arranged, when generating the three dimensional internal image of the part of the patient from the imaging system, such that the fiducial marker members are visible in generating the three dimensional internal image;
   the control system being arranged to provide, from the robot when the robot is in position for operating on the patient, inputs of the position of the tool relative to the fiducial marker members, whereby the position of the tool is located and displayed on the three dimensional internal image of the part of the patient.

13. Apparatus for use in surgical procedures on a patient comprising:
   a magnetic resonance imaging system for obtaining a three dimensional internal image through a part of the body of the patient;
   the magnetic resonance imaging system including a magnet having a horizontal bore open at least at one end for receiving the part of the body of the patient therein;
   a robot for operating on the part of the body of the patient, the robot including:
   a movable support assembly arranged to be located in fixed position adjacent the bore of the magnet;
   at least one movable arm carried on the support assembly for extending into the bore;
   said at least one arm having a plurality of joints and drive motors therefor defining at least four degrees of freedom of movement of the arm;
   said at least one arm having an end effector for carrying a selected surgical tool for operation on the patient;
   said at least one arm being arranged such that in use the joints and the motors extend into the bore to allow dextrous manipulation of the tool within the bore to change an angle of an axis of the tool in the bore relative to an axis of the bore and relative to the patient;
   at least one camera arranged to be located at a position for obtaining a visual image of the part of the patient;
   and a workstation and control system including:
   at least one hand-controller to be manipulated by an operator to control movement of said at least one arm;
   a first display for displaying the visual image obtained from the at least one camera;
   a second display for displaying the three dimensional internal image obtained from the magnetic resonance imaging system of the part of the patient and for displaying on the three dimensional internal image the real-time location of the surgical tool;
   wherein the robot is MR compatible in that the joints and motors of the arm can work within me confines of the high magnetic fields of the magnet of the MRI system without being affected by the MRI electromagnetic field emissions and without affecting the quality of the MRI imaging.

14. The apparatus according to claim 13 wherein said at least one arm comprises two arms and wherein a first one of the arms is arranged such that said first arm can be moved relative to the support to a deployed position and a second one of the arms can be moved relative to the support to a retracted position to allow said first arm only to extend into the bore with the support located at one end of the bore.

15. The apparatus according to claim 14 wherein the support includes a movable slide table forming an extension thereof onto which the first arm can be moved.

16. The apparatus according to claim 13 wherein each joint providing a respective degree of freedom is driven by a piezoelectric ultrasonic motor.

17. The apparatus according to claim 13 wherein each joint provides for rotation about either a vertical or a horizontal axis.

18. The apparatus according to claim 17 wherein those joints which provide rotation about a horizontal axis are arranged to minimize the moment of those portions of the arm which cantilevered from that joint so as to minimize the force necessary on the joint to counteract gravity.

19. The apparatus according to claim 17 wherein some of the joints include a single piezoelectric motor and some include two piezoelectric motors for increased torque.

20. Apparatus for use in surgical procedures on a patient comprising:
   an imaging system for obtaining a three dimensional internal image through a selected part of the body of the patient;

a robot for operating on the part of the body of the patient, the robot including:
a movable support assembly arranged to be located in fixed position adjacent the patient;
at least one movable arm carried on the support assembly;
said at least one arm having a plurality of degrees of freedom of movement;
said at least one arm having an end effector for carrying a selected surgical tool for operation on the patient;
at least one camera arranged to be located at a position for obtaining a visual image of the part of the patient;
and a workstation and control system including:
at least one hand-controllers to be manipulated by an operator to control movement of said at least one arm;
a first display for displaying the visual image obtained from the at least one camera;
a second display for displaying the three dimensional internal image obtained from an imaging system of the part of the patient;
wherein the at least one camera includes a microscope having two optical viewing channels each having a respective one of two high definition cameras;
wherein the first display for displaying at least one image from the microscope includes a monitor for viewing an enlarged two dimensional image from the microscope end a two channel microscope viewing system for viewing stereoscopic images from the microscope.

21. Apparatus for use in surgical procedures on a patient comprising:
a robot for operating on the part of the body of the patient, the robot including:
a movable support assembly arranged to be located in fixed position adjacent the patient;
at least one movable arm carried on the support assembly;
said at least one arm having a plurality of degrees of freedom of movement;
said at least one arm having an end effector for carrying a selected surgical tool for operation on the patient;
at least one camera arranged to be located at a position for obtaining a visual image of the part of the patient;
and a workstation and control system including:
at least one hand-controller to be manipulated by an operator to control movement of said at least one arm;
a first display for displaying the visual image obtained from the at least one camera;
the at least one hand-controller having force feedback sensors arranged to be controlled in response to the detected forces for providing haptic effect to the operator;
wherein the force sensors for detecting forces applied to the tool by engagement with the part of the patient include a first sensor for detecting forces in an axial (Z) direction along the tool and a second and third sensor for detecting transverse forces on the tool in the X and Y planes.

22. The apparatus according to claim 21 wherein the end-effector of each arm includes a roll actuator for causing roll movements of the tool about a longitudinal axis of the tool and a tool actuator for causing actuation movements of the tool and wherein the first force sensor is located on the roll actuator and the second force sensor is located on the tool actuator.

23. The apparatus according to claim 21 wherein the force sensors are optical force sensors.

* * * * *